United States Patent
Amsen et al.

(10) Patent No.: US 12,180,458 B2
(45) Date of Patent: Dec. 31, 2024

(54) METHOD FOR DETECTING CD4+CD25+GLYCOPROTEIN A33(GPA33)HIGH AND/OR CD4+CD127-GPA33HIGH T CELLS

(71) Applicants: Stichting Sanquin Bloedvoorziening, Amsterdam (NL); Stichting Het Nederlands Kanker Instituut-Antoni van Leeuwenhoek Ziekenhuis, Amsterdam (NL)

(72) Inventors: Derk Amsen, Amsterdam (NL); Eloy Cuadrado Godia, Amsterdam (NL); Jannetje Geertruida Borst, Amsterdam (NL)

(73) Assignees: Stichting Sanquin Bloedvoorziening, Amsterdam (NL); Stichting Het Nederlands Kanker Institmit-Antoni van Leeuwenhoek Ziekenhuis, Amsterdam (NL)

( * ) Notice: Subject to any disclaimer, the term of this patent is extended or adjusted under 35 U.S.C. 154(b) by 498 days.

(21) Appl. No.: 16/499,599

(22) PCT Filed: Mar. 29, 2018

(86) PCT No.: PCT/EP2018/058211
§ 371 (c)(1),
(2) Date: Sep. 30, 2019

(87) PCT Pub. No.: WO2018/178296
PCT Pub. Date: Oct. 4, 2018

(65) Prior Publication Data
US 2020/0101107 A1    Apr. 2, 2020

(30) Foreign Application Priority Data

Mar. 29, 2017  (EP) .................... 17163525

(51) Int. Cl.
| | |
|---|---|
| *A61P 37/06* | (2006.01) |
| *A61K 35/12* | (2015.01) |
| *A61K 39/00* | (2006.01) |
| *C12N 5/0783* | (2010.01) |
| *G01N 33/50* | (2006.01) |

(52) U.S. Cl.
CPC ........ *C12N 5/0637* (2013.01); *A61K 39/4611* (2023.05); *A61K 39/4621* (2023.05); *A61K 39/46433* (2023.05); *A61P 37/06* (2018.01); *G01N 33/505* (2013.01); *A61K 2035/122* (2013.01)

(58) Field of Classification Search
None
See application file for complete search history.

(56) References Cited

U.S. PATENT DOCUMENTS

2016/0169891 A1  6/2016  Gorochov et al.
2016/0194398 A1  7/2016  Wang et al.

FOREIGN PATENT DOCUMENTS

| WO | 2007/117602 A2 | 10/2007 |
| WO | 2008101272 A1 † | 8/2008 |
| WO | 2015/014871 A1 | 2/2015 |

OTHER PUBLICATIONS

Junichi Sakamoto et al., "Organ-specific expression of the intestinal epithelium-related antigen A33, a cell surface target for antibody-based imaging and treatment in gastrointestinal cancer", Cancer Chemother. Pharmacol. (2000) 46 (Suppl), S27-S32.
Jeffrey A. Bluestone et al., "Type 1 diabetes immunotherapy using polyclonal regulatory T cells", www.ScienceTranslationalMedicine.org, Nov. 25, 2015, vol. 7, Issue 315, 315ra189 pp. 1-14.
Megan E. Himmel et al., "Helios+ and Helios− Cells Coexist within the Natural FOXP3 +T Regulatory Cell Subset in Humans", J. Immunol. 2013; 190:2001-2008.
Pervinder Sagoo et al., "Human Regulatory T Cells with Alloantigen Specificity Are More Potent Inhibitors of Alloimmune Skin Graft Damage than Polyclonal Regulatory T Cells", www.ScienceTranslationalMedicine.org May 18, 2011, vol. 3, Issue 83, 83ra42 pp. 1-10.
Keli L. Hippen et al., "Massive ex vivo expansion of human natural regulatory T cells (Tregs) with minimal loss of in vivo functional activity", Sci. Trans. Med., May 18, 2011, 3(83), 83ra41, pp. 1-16.
Angela M. Thornton et al., "Expression of Helios, an Ikaros Transcription Factor Family Member, Differentiates Thymic-Derived from Peripherally Induced Foxp3 + T Regulatory Cells", J. Immunol. 2010, 184:3433-3441.
Joan K. Heath et al., "The human A33 antigen is a transmembrane glycoprotein and a novel member of the immunoglobulin superfamily", Proc. Natl. Acad. Sci. USA, vol. 94, pp. 469-474, Jan. 1997.
Piotr Trzonkowski et al., "Hurdles in therapy with regulatory T cells", www.ScienceTranslationalMedicine.org, Sep. 9, 2015, vol. 7, Issue 304, 304ps18, pp. 1-10.

† cited by third party

*Primary Examiner* — Amy E Juedes
(74) *Attorney, Agent, or Firm* — Pillsbury Winthrop Shaw Pittman, LLP

(57) ABSTRACT

The invention relates to isolated populations of CD4+ GPA33$^{high}$ regulatory T cells, to methods for detecting and/or isolating CD4+GPA33$^{high}$ cells, methods for enriching for CD4+GPA33$^{high}$ cells and to uses of CD4+GPA33$^{high}$ cells and populations of such cells. The invention further relates to methods for classifying an individual suffering from cancer and typing a tumor sample as well as for determining the etiology of autoimmune diseases.

10 Claims, 17 Drawing Sheets

METHOD FOR DETECTING CD4+CD25+GLYCOPROTEIN A33(GPA33)HIGH AND/OR CD4+CD127-GPA33HIGH T CELLS

CROSS-REFERENCE TO RELATED APPLICATIONS

This application is the U.S. national stage entry of PCT/EP2018/058211, filed Mar. 29, 2018, which claims priority to: European Patent Application No. 17163525.3, filed Mar. 27, 2017, the entire contents of each of which are herein incorporated by reference in their entireties.

FIELD OF THE INVENTION

The invention relates to populations of stable regulatory T cells, to uses thereof and to methods for identifying, quantifying and isolating regulatory T cells.

BACKGROUND OF THE INVENTION

The immune system protects our body against foreign invaders and conventional CD4 T cells (Tconv) are important in this defence function. The immune system must however carefully be held in check, to prevent it from turning on the very body it is supposed to protect (during autoimmune disease) or from attacking harmless or even useful micro-organisms (such as the bacteria in our intestines). Major controllers of the immune system are a second type of CD4 T cells, known as regulatory T cells (Tregs). Tregs suppress immunity and as such are critical for immune tolerance, prevention of excessive immunity and tissue repair.

The identity of a Treg is installed by the transcription factor Foxp3. There are two fundamentally different types of Tregs. The thymic (t) Treg arises from positive selection of self-reactive CD4 T cells during T cell development in the thymus. tTregs are stably committed to Foxp3 expression and the Treg fate and constitute a separate lineage from conventional T cells. A second type of Tregs stems from mature CD4 Tconvs that during their response to (foreign) antigen have gained Foxp3 expression and are converted into Tregs. These peripherally induced Tregs (iTregs) are unstable. When exposed to inflammatory signals, iTregs can lose Foxp3 expression and resume Tconv identity and function.

There are major efforts world wide to use Tregs for treatment of autoimmune diseases (such as Type I diabetes and multiple sclerosis) and to prevent rejection of organ transplants. To this end, Tregs are isolated from donors, expanded in vitro, and injected into patients. There are currently no markers that allow discrimination between (stable) tTregs and (unstable) iTregs. Generally, Tregs are currently isolated from CD4$^+$ T cells, based on high expression of CD25 and absence of CD127. These isolation criteria result in inclusion of contaminating conventional CD4$^+$ T cells, particularly because the expression profile of CD127 is not sufficiently discriminatory to rigorously exclude Tconvs. Furthermore, the CD127$^-$CD25$^{high}$ population of Tregs contains a mixture of stable tTregs and unstable iTregs, the latter of which can differentiate into Tconvs under the influence of inflammatory signals. Both the presence of Tconvs and of unstable Tregs pose a risk in therapies in which Tregs are adoptively transferred into patients, as these cells may attack the recipient.

A number of markers for functional Tregs has been identified, including CD39, LAP and GARP. These markers are found on activated Tregs and there is no evidence that they distinguish between stable and unstable Tregs.

In addition, one of the challenges for adoptive cellular therapy with Tregs is that sorted Treg populations are not stable: during in vitro expansion, contaminating Tconv can overgrow Tregs and iTregs can lose their Treg identity. To circumvent this problem, Tregs are currently expanded in the presence of the drug rapamycin, which blocks growth of conventional T cells, but still permits survival and growth of Tregs. However, despite the relative tolerance of Tregs to rapamycin, inclusion of this drug suppresses the expansion rate of Tregs and may alter their functional properties. Moreover, after infusion into patients, no rapamycin is available to maintain selective pressure.

Thus, currently used markers are not sufficient to allow purification of pure stable Tregs and the Treg preparations therefore include cells that may develop harmful activity against the recipient. Therefore, there remains a need for improved methods for isolation, purification and identification of stable Tregs, in particular that maintain regulatory T cell function after expansion in vitro.

SUMMARY OF THE INVENTION

It is an object of the present invention to provide stable regulatory T cell populations, in particular of Tregs that maintain their regulatory T cell function after expansion in vitro and after administration to patients. It is a further object of the invention to provide improved methods for identification, isolation, purification and/or enrichment of stable Tregs. These Tregs are for instance suitable for use in adoptive immunotherapy. It is a further object of the present invention to provide method wherein such stable Tregs are used in prognosis and/or diagnosis of diseases and treatment response, in particular in cancer and autoimmune disease.

The invention therefore provides a method for enriching a population of cells for regulatory T cells comprising:
a. contacting a population of cells with an agent capable of binding GPA33,
b. determining binding of said cells to said agent capable of binding GPA33, and
c. selecting and/or isolating CD4$^+$ T cells that have a level of expression of GPA33 that is higher than the average level of expression of GPA33 in said population of cells.

Also provided is a method for enriching a population of cells for regulatory T cells comprising:
a. contacting a population of cells with an agent capable of binding CD4 and an agent capable of binding GPA33, and
b. determining binding of said cells to said agents capable of binding CD4 and GPA33,
c. selecting and/or isolating cells that bind to said agent capable of binding CD4 and that have a level of expression of GPA33 that is higher than the average level of expression of GPA33 in said population of cells.

Said regulatory T cells are preferably stable regulatory T cells. It is further preferred that cells are selected and/or isolated that have a level of expression of GPA33 that is higher than the average level of expression of GPA33 in CD4$^+$ cells present in said population of cells. It is further preferred that CD4$^+$ cells are selected and/or isolated that have a level of expression of GPA33 that is higher than the average level of expression of GPA33 in CD4$^+$ T cells.

Hence, a population of cells preferably comprises T cells, more preferably CD4+ T cells. Said T cells, more preferably CD4+ T cells, are preferably obtained from mammalian blood, synovial fluid or lymph, wherein said blood is preferably cord blood or peripheral blood. It is further preferred that the cells that are selected and/or isolated are CD4+CD25+CD127−GPA33$^{high}$ or CD4+CD25+CD127$^{low}$GPA33$^{high}$ cells. Hence, it is preferred that the population of cells is further contacted with an agent capable of binding CD25 and an agent capable of binding CD127 and that cells are selected and/or isolated that bind to the agent capable of binding CD25 and essentially do not bind to the agent capable of binding CD127 or show low binding to the agent capable of binding CD127.

In a further aspect, the invention provides a method for isolating regulatory T cells, the method comprising isolating CD4+GPA33$^{high}$ T cells from a cell sample. Said regulatory T cells are preferably stable regulatory T cells. It is further preferred that the cells that are isolated are CD4+CD25+CD127−GPA33$^{high}$ or CD4+CD25+CD127$^{low}$GPA33$^{high}$ cells.

In a further aspect, the invention provides a method for identifying regulatory T cells comprising analyzing CD4+ T cells for expression of GPA33, wherein a CD4+GPA33$^{high}$ expression pattern is indicative of a regulatory T cell or a population of regulatory T cells. Preferably expression of CD25 is further analyzed and a CD4+CD25+GPA33$^{high}$ expression pattern is indicative of a regulatory T cell or a population of regulatory T cells.

Also provided is a method for identifying regulatory T cells comprising analyzing cells for expression of CD4 and GPA33, wherein a CD4+GPA33$^{high}$ expression pattern is indicative of a regulatory T cell or a population of regulatory T cells. Said regulatory T cells are preferably stable regulatory T cells. It further is preferred that the cells that are isolated are CD4+CD25+CD127−GPA33$^{high}$ or CD4+CD25+CD127$^{low}$GPA33$^{high}$ cells.

In a further aspect, the invention provides a method for detecting regulatory CD4+ T cells comprising analyzing cells for expression of GPA33, wherein a CD4+GPA33$^{high}$ expression pattern is indicative of a regulatory T cell or a population of regulatory T cells. Also provided is a method for detecting regulatory T cells comprising analyzing cells for expression of CD4 and GPA33, wherein a CD4+GPA33$^{high}$ expression pattern is indicative of a regulatory T cell or a population of regulatory T cells. Said regulatory T cells that are detected are in one embodiment stable regulatory T cells and the presence of CD4+GPA33$^{high}$ cells is indicative of stable regulatory T cells It further is preferred that the cells that are detected are CD4+CD25+CD127−GPA33$^{high}$ or CD4+CD25+CD127$^{low}$GPA33$^{high}$, which expression pattern is indicative of a regulatory T cell or a population of regulatory T cells.

In a further aspect, the invention provides a population of cells isolated or obtained with a method according to the invention.

In a further aspect, the invention provides an isolated population of cells wherein at least 75% of the cells are CD4+GPA33$^{high}$ regulatory T cells.

In a further aspect, the invention provides a pharmaceutical composition comprising a population of regulatory T cells according to the invention and a pharmaceutically acceptable carrier, diluent and/or excipient.

In a further aspect, the invention provides a method for detecting 10 regulatory T cells in a sample, said method comprising detecting whether CD4+GPA33$^{high}$ cells are present in the sample by contacting the sample with an anti-CD4 antibody or antigen-binding fragment thereof and an anti-GPA33 antibody or antigen-binding fragment thereof and detecting binding between cells in said sample and said anti-CD4 antibody or antigen-binding fragment thereof and said anti-GPA33 antibody or antigen-binding fragment thereof.

In a further aspect, the invention provides a use of GPA33 as a marker for regulatory T cells.

In a further aspect, the invention provides CD4+GPA33$^{high}$ T cells or a population of cells according to the invention for use in therapy. Said cells preferably are, and said population of cells preferably comprises at least 75% of CD4+CD25+CD127−GPA33$^{high}$ or CD4+CD25+CD127$^{low}$GPA33$^{high}$ cells.

In a further aspect, the invention provides CD4+GPA33$^{high}$ T cells or a population of cells according to the invention for use in suppressing an immune response. Said cells preferably are, and said population of cells preferably comprises at least 75% of, CD4+CD25+CD127−GPA33$^{high}$ or CD4+CD25+CD127$^{low}$GPA33$^{high}$ cells.

In a further aspect, the invention provides CD4+GPA33$^{high}$ T cells or a population of cells according to the invention for use in the treatment, alleviation or prevention of graft versus host disease (GVHD), transplant rejection, a chronic inflammatory condition or an autoimmune disease. Said cells preferably are, and said population of cells preferably comprises at least 75% of, CD4+CD25+CD127−GPA33$^{high}$ or CD4+CD25+CD127$^{low}$GPA33$^{high}$ cells.

In a further aspect, the invention provides a method for suppressing an immune response in a subject in need thereof comprising administering to the subject a therapeutically effective amount of CD4+GPA33$^{high}$ T cells, a population of cells according to the invention or a pharmaceutical composition according to the invention. Said cells preferably are, and said population of cells preferably comprises at least 75% of, CD4+CD25+CD127−GPA33$^{high}$ or CD4+CD25+CD127$^{low}$GPA33$^{high}$ cells.

In a further aspect, the invention provides a method for treatment, alleviation or prevention of graft versus host disease (GVHD), transplant rejection, a chronic inflammatory condition or an autoimmune disease, the method comprising administering to a subject in need thereof CD4+GPA33$^{high}$ T cells or a population of cells according to the invention. Said cells preferably are, and said population of cells preferably comprises at least 75% of, CD4+CD25+CD127−GPA33$^{high}$ or CD4+CD25+CD127$^{low}$GPA33$^{high}$ cells.

In a further aspect, the invention provides a use of CD4+GPA33$^{high}$ T cells, a population of cells according to the invention or a pharmaceutical composition according to the invention for the preparation of a medicament for suppressing an immune response in a subject in need thereof. Said cells preferably are, and said population of cells preferably comprises at least 75% of, CD4+CD25+CD127−GPA33$^{high}$ or CD4+CD25+CD127$^{low}$GPA33$^{high}$ cells.

In a further aspect, the invention provides a use of CD4+GPA33$^{high}$ T cells or a population of cells according to the invention for the preparation of a medicament for the treatment, alleviation or prevention of graft versus host disease (GVHD), transplant rejection, a chronic inflammatory condition or an autoimmune disease. Said cells preferably are, and said population of cells preferably comprises at least 75% of, CD4+CD25+CD127−GPA33$^{high}$ or CD4+CD25+CD127$^{low}$GPA33$^{high}$ cells.

In a further aspect, the invention provides a method for classifying an autoimmune disease as an autoimmune disease characterized by regulatory T cell insufficiency, the method comprising quantifying the level of CD4$^+$GPA33$^{high}$ cells in a sample from an individual suffering from an autoimmune disease in accordance with a method and comparing said level with the level of CD4$^+$GPA33$^{high}$ cells in a reference sample, preferably wherein said reference sample is a sample from a healthy individual. Preferably, the method comprises quantifying the level of CD4$^+$CD25$^+$ GPA33$^{high}$ cells in a sample from an individual suffering from an autoimmune disease in accordance with a method and comparing said level with the level of CD4$^+$CD25$^+$ GPA33$^{high}$ cells in a reference sample, preferably wherein said reference sample is a sample from a healthy individual.

In a further aspect, the invention provides a use of GPA33 as a marker for prognosis in cancer.

In a further aspect, the invention provides a method for classifying an individual suffering from cancer as having a poor prognosis or a good prognosis, the method comprising:
  a) determining the level of CD4$^+$CD25$^+$GPA33$^{high}$ T cells in a tumor sample
  b) determining the level of CD4$^+$CD25$^+$GPA33$^{high}$ T cells in a reference sample, and
  c) comparing the level of CD4$^+$CD25$^+$GPA33$^{high}$ T cells in said tumor sample determined in a) with the level of CD4$^+$CD25$^+$GPA33$^{high}$ T cells in said reference sample determined in b),
wherein a level of CD4$^+$CD25$^+$GPA33$^{high}$ T cells in said tumor sample that is higher than the level of CD4$^+$CD25$^+$ GPA33$^{high}$ T cells in said reference sample is indicative of a poor prognosis.

In a further aspect, the invention provides a method for typing a tumor sample of an individual suffering from cancer, the method comprising:
  a) determining a level of CD4$^+$CD25$^+$GPA33$^{high}$ T cells in a tumor sample
  b) determining a level of CD4$^+$CD25$^+$GPA33$^{high}$ T cells in a reference sample, and
  c) typing said tumor sample on the basis of the levels of CD4$^+$CD25$^+$GPA33$^{high}$ T cells determined in said tumor sample and said reference sample.

In a further aspect, the invention provides a method for predicting response to therapy in an individual suffering from cancer, the method comprising:
  a) determining a level of CD4$^+$CD25$^+$GPA33$^{high}$ T cells in a tumor sample
  b) determining a level of CD4$^+$CD25$^+$GPA33$^{high}$ T cells in a reference sample, and
  c) comparing the level of CD4$^+$CD25$^+$GPA33$^{high}$ T cells in said tumor sample with the level of CD4$^+$CD25$^+$ GPA33$^{high}$ T cells in said reference sample,
wherein a level of CD4$^+$CD25$^+$GPA33$^{high}$ T cells in said tumor sample that is higher than the level of CD4$^+$CD25$^+$ GPA33$^{high}$ T cells in said reference sample is indicative of a poor response to therapy.

DETAILED DESCRIPTION

Tregs can be characterized by cell surface markers. The majority of Tregs express CD4 and high levels of CD25 (interleukin-2 receptor alpha chain). In addition, the absence or low-level expression of CD127 in combination with the presence of CD4 and CD25 expression is used as a marker for Tregs. Further, Tregs are characterized by expression of forkhead family transcription factor box p3 (Foxp3). FoxP3 is a transcription factor that governs the Treg lineage. All Tregs express this factor and its stable expression is critical for Treg function. Loss of FoxP3 expression results in conversion to conventional T cells. A second transcription factor associated with Tregs is Helios. Not all Tregs express this transcription factor, however. In mouse Tregs, expression of Helios marks stable tTregs. However, in human Tregs, expression of Helios can be induced in Helios Tregs upon activation, making it an unreliable marker for tTregs on its own. Expression of these transcription factors cannot be used to isolate viable Tregs for adoptive immunotherapy. As these molecules reside inside the cells, their detection requires permeabilization of the cell membrane and fixation of the cells, procedures that are inconsistent with viability.

The present inventors have identified the cell surface molecule glycoprotein A33 (GPA33) as a marker for a subset of regulatory T cells, in particular for CD4$^+$ regulatory T cells. It has been found that GPA33 is selectively highly expressed on stable regulatory T cells, and not on other types of T cells, including conventional CD4$^+$ T cells and induced Tregs.

As used herein "conventional T cells" refers collectively to all T cells that activate the immune systems, including e.g. helper T cells, cytotoxic T cells and memory T cells. The term "conventional CD4$^+$ T cells" refers to such conventional T cells that express CD4 on their cell surface. The terms regulatory T cells, Treg cells and Tregs are used interchangeably herein. As described herein before, T cells, including Tregs, can be characterized by the presence and/or absence of cell surface markers. Presence of a cell surface marker on a T cell, such as a Treg, is also referred to as expression of the marker on the T cell, i.e. the T cell expresses the marker. A "cell surface marker" as used herein refers to an antigenic determinant or epitope present on the surface of a specific type of cell, such as a conventional T cell or a Treg cell. Similarly, "expressing" or "expression" of a marker refers to the presence of such antigenic determinant or epitope on the surface of a specific type of cell. Cell surface markers can be targeted with agents which bind thereto. Thus, cell surface markers can be recognized and detected via an antigenic determinant or epitope found on the surface of a specific type of cell by agents that specifically bind to the cell surface markers. For example, markers on the surfaces of cells can be bound by antibodies specific for the particular marker.

As used herein, the term "stable Tregs" refers to Tregs that are committed to their fate as Tregs and do not differentiate into a T cell type other than Tregs under the influence of environmental factors or changes, such as under the influence of IL-1, IL-6 and/or TNFα. These stable Tregs are herein also referred to as thymic Tregs or tTregs, as they are thought to typically originate from the thymus, although they are not limited to thymic derived stable Tregs. The fact that these stable Tregs remain Tregs is for instance evidenced by the continued expression of FOXP3 and Helios. Hence, stable Tregs or tTregs as used herein are T cells that are FOXP3$^+$Helios$^+$. As used herein, the term "unstable Tregs" refers to Tregs that have been generated as conventional T cells, in particular conventional CD4$^+$ T cells, and which have been converted or induced into Tregs outside the thymus. These unstable Tregs are therefore also referred to as induced Tregs or iTregs. Unlike tTregs, these iTregs are not irreversibly committed to the Treg cell type: they can resume conventional T cell function, e.g. under the influence of environmental factors such as inflammatory signals (such as IL-1, IL-6 and TNFα). Once these iTregs resume conventional T cell function they no longer express FOXP3.

As described above, the present inventors have identified a cell surface marker, GPA33, that can be used to distinguish stable Tregs (or tTregs) from unstable Tregs (or iTregs).

Using this marker, a population of stable Tregs, that are characterized by a high expression of GPA33, can be identified and obtained, whereas with currently used strategies, which are based on the markers CD4, CD25 and CD127, a mixture of stable Tregs and unstable Tregs is obtained. As indicated above, the latter can resume conventional T cell function under the influence of e.g. proinflammatory factors. Such factors are present inside a patient's body following administration, especially since treated patients often exhibit inflammatory diseases. Hence, unstable Tregs present in a population of Tregs isolated using currently known markers may result in the presence and/or development of conventional T cells activating the immune system in a patient, which is undesirable in therapy aimed at suppression of an immune response. Moreover, during expansion of T cells in vitro, conventional T cells generally proliferate more rapidly than Tregs. As a result, the ratio of Tregs to conventional T cells gradually decreases during expansion. Thus, even trace amounts of conventional T cells in the starting population can be expanded in high cell numbers, i.e. Tregs may be overgrown by conventional T cells. Currently, Tregs are expanded in the presence of rapamycin, which suppresses growth of conventional T cells, but may also negatively influence growth and other properties of Tregs. It is therefore highly desirable to start expansion in vitro with a population as pure in stable Tregs as possible. By isolating GPA33$^{high}$ expressing CD4$^+$ T cells in accordance with the present invention both conventional CD4 T cells and unstable Tregs can be minimized. In addition, selection of Tregs based on high GPA33 expression obviates the need for expansion of Tregs in the presence of rapamycin, a compound that negatively influences the expansion rate of Tregs and their functional properties.

GPA33 is a transmembrane protein which is expressed in normal gastrointestinal epithelium. It has been found to be expressed in 95% of colon cancers. The mature protein has a 213-amino acid extracellular region, a transmembrane domain, and a 62-amino acid intracellular tail. GPA33 extracellularly contains an Ig-like C2-type domain and an Ig-like V-type domain, which is characteristic of the CD2 subgroup of the immunoglobulin superfamily. GPA33 may play a role in cell-cell recognition and signaling. Expression of GPA33 on T cells has not been previously reported. Moreover, it has not been previously recognized as a marker of T cells in general or of a specific subset of T cells. Antibodies against GPA33 are commercially available, for instance from Abcam, Sigma-Aldrich, Novus Biologicals, R&D Systems and LifeSpan BioSciences. In addition, an antibody against GPA33 is described in Heath, J. K., et al. 1997.

In a first aspect the invention provides an isolated population of cells wherein at least 75% of the cells are CD4$^+$ GPA33$^{high}$ regulatory T cells. Such population is herein also referred to as a population of regulatory T cells according to the invention, as a population of Tregs according to the invention or as a population according to the invention. A "population of regulatory T cells" or a "population of cells wherein at least 75% of the cells are CD4$^+$GPA33$^{high}$ regulatory T cells" as used herein refers to a plurality of regulatory T cells (Tregs). Preferably, a population comprises at least 100 Tregs, more preferably at least $10^3$, $10^4$, $10^5$, $10^6$, $10^7$, $10^8$, $10^9$, $10^{10}$, or $10^{11}$ Tregs. A population of cells in particular embodiments comprises at least $10^5$ Tregs, such as from $10^5$ to $10^7$ Tregs, from $10^6$ to $10^8$ Tregs, or from $10^5$ to $10^{11}$ Tregs. Any source that contains T cells can be used to isolate Tregs expressing CD4 and GPA33 to obtain an isolated population of Tregs according to the invention. Preferably, the population is obtained from blood, such as peripheral blood or cord blood, or from synovial fluid or lymph. However, the population of Tregs according to the invention can also be obtained from a tissue such as thymus, spleen, lymph nodes, bone marrow and Peyer's patches or from neonatal umbilical cord blood.

"Isolated" as used herein refers to Tregs that are removed from their natural environment. Preferably, it refers to a Treg population which has been separated or purified from other components, including other cell types, such as components present in body fluids such as blood, synovial fluid or lymph or in tissue.

An isolated population of cells according to the invention comprises at least 75% CD4$^+$GPA33$^{high}$ regulatory T cells. Typically, in humans about 1-5% of circulating CD4$^+$ T cells are Tregs, of which approximately 40% are stable tTregs. With currently used methods based on expression of CD4, expression of CD25 and lack or low level of CD127 expression both stable and unstable Tregs are isolated. Hence, a population of cells according to the invention is enriched in Tregs and in stable tTregs as compared to (human) blood and as compared to populations of Tregs that are isolated with conventional methods. An isolated population of cells according to the invention preferably comprises at least 80% CD4$^+$GPA33$^{high}$ regulatory T cells, more preferably at least 85% CD4$^+$GPA33$^{high}$ regulatory T cells, more preferably at least 90% CD4$^+$GPA33$^{high}$ Tregs, more preferably at least 95% CD4$^+$GPA33$^{high}$ Tregs, more preferably at least 98% CD4$^+$GPA33$^{high}$ Tregs, more preferably at least 99% CD4$^+$ GPA33$^{high}$ Tregs. In a preferred embodiment, essentially all cells in a population of Tregs according to the invention are Tregs that express high GPA33. In a further embodiment, all cells in a population of Tregs according to the invention are Tregs that express high GPA33.

An isolated population of cells according to the invention comprises less than 25% non-stable regulatory T cells (non-Tregs), i.e. cells other than CD4$^+$GPA33$^{high}$ Tregs. As used herein the term "non-stable regulatory T cells" refers to any type of cell other than stable regulatory T cells as defined herein, including other types of T cells, such as conventional CD4$^+$ T cells or conventional CD8$^+$ T cells, but also other cell types, such as macrophages, monocytes, neutrophils, endothelial cells, etc. Preferably, a population of CD4$^+$ GPA33$^{high}$ Tregs according to the invention comprises less than 20% cells other than CD4$^+$GPA33$^{high}$ Tregs, more preferably less than 15% cells other than CD4$^+$GPA33$^{high}$ Tregs, more preferably less than 10% cells other than CD4$^+$GPA33$^{high}$ Tregs, more preferably less than 5% cells other than CD4$^+$GPA33$^{high}$ Tregs, more preferably less than 2% cells other than CD4$^+$GPA33$^{high}$ Tregs, more preferably less than 1% cells other than CD4$^+$GPA33$^{high}$ Tregs. In a preferred embodiment, a population of Tregs according to the invention is essentially free of T cells other than CD4$^+$ GPA33$^{high}$ Tregs. In a further embodiment, a population of Tregs according to the invention is free of T cells other than CD4$^+$GPA33$^{high}$ Tregs.

The CD4$^+$GPA33$^{high}$ Tregs in a population according to the invention preferably express CD25. Further, the CD4$^+$ GPA33$^{high}$ Tregs are preferably CD127$^{low}$ or negative, which means that the Tregs do not express CD127 or have a low expression of CD127. Hence, in a preferred embodiment, a population of Tregs according to the invention comprises at least 75% CD4$^+$CD25$^+$CD127$^-$GPA33$^{high}$ cells or CD4$^+$CD25$^+$CD127$^{low}$GPA33$^{high}$ cells. Further, the CD4$^+$ GPA33$^{high}$ Tregs preferably also express FoxP3. Hence, in a preferred embodiment, a population of cells according to the invention comprises at least 75% CD4$^+$GPA33$^{high}$ FoxP3$^+$ cells, more preferably CD4$^+$CD25$^+$CD127$^-$GPA33$^{high}$FoxP3$^+$ cells or CD4$^+$GPA33$^{high}$CD25$^+$CD127$^{low}$FoxP3$^+$ cells.

The terms "+", "−", "low" and "high" in the context of cell surface markers or intracellular markers, in particular to T cells, are well known in the art. It refers to the level of expression of a particular marker.

In particular, the term "+" refers to the presence of a particular marker on the surface of a cell or in the cells. For instance, the term "CD4+" indicates that a cell expresses CD4 on its surface.

The term "−" refers to the absence of a particular marker on the surface of a cell or in the cells. For instance, the term "CD127$^-$" indicates that a cell does not express CD127 on its surface.

The term "low" refers to a level of expression of a particular marker by a cell or population of cells within or isolated from a sample that is absent or relatively low when compared to the level of expression of the marker on other cells in a population or in the sample from which the population of cells is obtained or as compared to the population of cells in such sample as a whole. For example, the term "CD127$^{low}$" refers to a level of expression of CD127 by a cell or population of cells that is absent or low as compared to the average level of expression of CD127 by cells in the population of cells in the sample that is analyzed or from which the population of cells is obtained. Preferably, "CD127$^{low}$" refers to a level of expression of CD127 that is at least 2-fold lower than the average level of expression of CD127 on CD4$^+$ T cells in the population of cells that is analyzed or from which the population of cells is obtained, more preferably at least 5-fold lower than the average level of expression of CD127 on CD4$^+$ T cells in the population of cells that is analyzed or from which the population of cells is obtained, at least 8-fold lower than the average level of expression of CD127 on CD4$^+$ T cells in the population of cells that is analyzed or from which the population of cells is obtained, such as about 10-fold lower than the average level of expression of CD127 on CD4$^+$ T cells in the population of cells that is analyzed or from which the population of cells is obtained.

The term "high" in this context is also well known in the art. It refers to a level of expression of a particular marker, such as CD4 or GPA33, by a cell or population of cells within or isolated from a sample that is relatively high when compared to the level of expression of the marker on other cells in the population or in the sample from which the population of cells is obtained or as compared to the population of cells in such sample as a whole. The term "GPA33$^{high}$" refers to a level of expression of GPA33 by a cell or population of cells that is high as compared to the average level of expression of GPA33 in the population of cells in the sample that is analyzed or from which the population of cells is obtained or as compared to the population of cells in such sample as a whole. Preferably, as used herein the term "GPA33$^{high}$" refers to a level of expression that is higher than the average level of expression of GPA33 on T cells, preferably CD4$^+$ T cells, in a blood sample of an individual, preferably a human individual. More preferably, "GPA33$^{high}$" refers to a level of expression that is at least 2-fold the average level of expression of GPA33 on CD4$^+$ T cells in a blood sample of a human individual or in the sample from which the CD4$^+$GPA33$^{high}$ cells are obtained, more preferably at least 5-fold the average level of expression of GPA33 on CD4$^+$ T cells in a blood sample of a human individual or in the sample from which the CD4$^+$GPA33$^{high}$ cells are obtained, more preferably at least 8-fold the average level of expression of GPA33 on CD4$^+$ T cells in a blood sample of a human individual or in the sample from which the CD4$^+$GPA33$^{high}$ cells are obtained, such as about 10-fold the average level of expression of GPA33 on CD4$^+$ T cells in a blood sample of a human individual or in the sample from which the CD4$^+$GPA33$^{high}$ cells are obtained. Typically, the term "GPA33$^{high}$" is further defined by the expression level of GPA33 at which 70% of CD4$^+$CD25$^+$CD45RA$^+$ T cells in the blood of a human individual are included.

Similarly, the term "cells that have a level of expression of GPA33 that is higher than the average level of expression of GPA33 in said population of cells" refers to a level of expression that is at least 2-fold higher than the average level of expression of GPA33 on CD4$^+$ T cells in said population of cells, more preferably at least 5-fold higher than the average level of expression of GPA33 on CD4$^+$ T cells in said population of cells, more preferably at least 8-fold higher than the average level of expression of GPA33 on CD4$^+$ T cells in said population of cells, such as about 10-fold higher than the average level of expression of GPA33 on CD4$^+$ T cells in said population of cells. In a preferred embodiment, said population of cells that is enriched for regulatory T cells comprises a blood sample, synovial fluid sample or lymph sample of an individual, preferably a human individual, and said level of expression of GPA33$^{high}$ cells is at least 2-fold the average level of expression of GPA33 on CD4$^+$ T cells in said blood, synovial fluid or lymph sample, more preferably at least 5-fold the average level of expression of GPA33 on CD4$^+$ T cells in said blood, synovial fluid or lymph sample, more preferably at least 8-fold the average level of expression of GPA33 on CD4$^+$ T cells in said blood, synovial fluid or lymph sample, such as about 10-fold higher than the expression of GPA33 on CD4+ T cells in said blood, synovial fluid or lymph sample.

Methods to determine the whether or not a surface marker is expressed on the surface of cells, and, if present, whether such expression is low or high are well known in the art. For example, expression of cell surface markers and expression levels thereof can be determined by flow cytometry using antibodies directed against the relevant cell surface markers, e.g. fluorescence activated cell sorting (FACS). Suitable methods are described in the Examples herein. Using such methods, the average expression level of all T cells in a sample as well as the expression level on specific subsets of T cells can be determined.

Stable Tregs in accordance with the invention show a high level of expression of GPA33, i.e. these cells are GPA33$^{high}$ cells.

A population of Tregs according to the invention is preferably a stable population of Tregs. A population of Tregs according to the invention is further preferably a viable population of Tregs.

Tregs in a population according to the invention are preferably immunosuppressive. In one embodiment the Tregs are immunosuppressive in vitro. In one embodiment the Tregs are immunosuppressive in vivo. Preferably the Tregs are immunosuppressive both in vitro and in vivo. As used herein the term "immunosuppressive" refers to the ability to reduce, weaken or prevent an immune response. For instance, the Tregs are immunosuppressive in that they, when administered to a subject, prevent the subject's immune system from mounting an immune response, e.g. after an organ or tissue transplant, reduce an immune response already initiated in a subject, e.g. in response to a disease that is caused by an overactive immune system such as an autoimmune disease or a chronic inflammatory disease.

In a further aspect, the invention provides a method for isolating regulatory T cells, the method comprising isolating CD4$^+$GPA33$^{high}$ T cells from a cell sample. The cells are preferably stable Tregs or tTregs, or have characteristics of stable or tTregs, including expression of FoxP3 and Helios and the fact that they remain stable after in vitro expansion, as evidenced by maintained expression of FoxP3 and Helios, optionally under the influence of environmental factors such as inflammatory signals (such as IL-1, IL-6 and TNFα). In addition, said cells are preferably characterized by the inability to produce the cytokines interferon γ (IFNγ), IL-2 and IL-17. A method for isolating Tregs, preferably stable Tregs, preferably comprises isolating CD4$^+$CD25$^+$CD127$^-$GPA33$^{high}$ or CD4$^+$CD25$^+$CD127$^{low}$GPA33$^{high}$ cells from the sample. GPA33$^{high}$ cells are for instance isolated using an agent that binds to GPA33. Similarly, CD4$^+$ cells are for instance isolated using an agent that binds to CD4. CD25$^+$CD127$^-$ or CD25$^+$CD127$^{low}$ cells are for instance isolated using an agent that binds to CD25 and an agent that binds to CD127. Isolation of cells positive for multiple markers can be performed at the same time for all markers or sequentially based on one or two markers at a time. In a particular embodiment, cells are selected first for CD4, and subsequently for CD25 expression, lack of or low expression of CD127 and high GPA33 expression. In a further particular embodiment, cells are selected first for absence of CD8 expression and presence of CD4 expression, and subsequently for presence of CD25 expression, absence of low level expression of CD127 and for high GPA33 expression.

In one embodiment, isolating regulatory T cells comprises preparing a population of regulatory T cells according to the invention.

Also provided is a method for enriching a population of cells for regulatory T cells comprising:
   a. contacting a population of cells with a an agent capable of binding GPA33,
   b. determining binding of said cells to said agent capable of binding GPA33, and
   c. selecting and/or isolating CD4$^+$ T cells that have a level of expression of GPA33 that is higher than the average level of expression of GPA33 in said population of cells.

The presence or absence of CD4 can be either determined directly by determining expression of CD4 on cells, e.g. by flow cytometry using an agent capable of binding CD4. Hence, in one embodiment, the method for enriching a population of cells for regulatory T cells comprises:
   a. contacting a population of cells with an agent capable of binding CD4 and an agent capable of binding GPA33,
   b. determining binding of said cells to said agents capable of binding CD4 and GPA33, and
   c. selecting and/or isolating cells that bind to the agent capable of binding CD4 and that have a level of expression of GPA33 that is higher than the average level of expression of GPA33 in said population of cells.

Alternatively, the presence or absence of CD4 can determined indirectly by depleting a population of cells, in particular if the population of cells comprises mammalian blood, synovial fluid or lymph cells, for cells other than CD4$^+$ T cells. In this embodiment, the population of cells is for instance depleted for erythrocytes and granulocytes by density gradient (f.i. using fycoll-Hypaque) and subsequently, e.g. by magnetic-activated cell sorting (MACS), for cells expressing CD8, CD11b, CD11c, CD14, CD16 and/or CD19 prior to contacting the population of cells with an agent capable of binding GPA33. The population of cells is further preferably depleted for CD127$^+$ T cells prior to contacting the population of cells with an agent capable of binding GPA33. Hence, in another embodiment, the method for enriching a population of cells for regulatory T cells comprises:
   a. depleting a population of cells from cells other than CD4$^+$ T cells,
   b. optionally depleting said population of cells from CD127$^+$ cells.
   c. contacting said population of cells with a an agent capable of binding GPA33,
   d. determining binding of said cells to said agent capable of binding GPA33, and
   e. selecting and/or isolating CD4$^+$ T cells that have a level of expression of GPA33 that is higher than the average level of expression of GPA33 in said population of cells. Said population of cells preferably comprises mammalian blood cells, synovial fluid cells or lymph cells.

Regulatory T cells for which the population of cells is enriched are GPA33$^{high}$ Tregs. The cells are thus preferably stable Tregs. It is further preferred that the cells that are selected and/or isolated are CD4$^+$CD25$^+$CD127$^-$GPA33$^{high}$ or CD4$^+$CD25$^+$CD127$^{low}$GPA33$^{high}$ cells. The cells preferably have the characteristics of stable Tregs (tTregs) defined herein, including expression of FoxP3 and Helios and the fact that they remain stable after in vitro expansion, as evidenced by maintained expression of FoxP3 and Helios, optionally under the influence of environmental factors such as inflammatory signals (such as IL-1, IL-6 and TNFα). In addition, said cells are preferably characterized by the inability to produce the cytokines interferon γ (IFNγ), IL-2 and IL-17. Said population of cells that is contacted with the agent capable of binding CD4 and the agent capable of binding GPA33 is preferably a cell sample as defined herein. In one embodiment, the population of cells is enriched for Tregs from umbilical cord blood, peripheral blood, peripheral mononuclear cells, lymph or synovial fluid. In another embodiment, the population of cells is enriched for Tregs from a tissue sample, such as a thymus, spleen or lymph node. "Enriching" or "enriched" as used herein with reference to population of cells, refers to an increased number of Tregs, preferably stable Tregs, in a population of cells as compared to the number of Tregs in a starting population of cells or in a sample comprising cells. The level of enrichment and/or percentage of purity of the Tregs will depend on factors including the starting population of cells or sample comprising cells, the donor from which the cells or sample is derived or obtained and body fluid or tissue source. Preferably, the CD4$^+$GPA33$^{high}$ Tregs, preferably stable Tregs, are enriched at least 2-fold, more preferably at least 5-fold, more preferably at least 10-fold, more preferably at least 20-fold, more preferably at least 30-fold, more preferably at least 40-fold, more preferably at least 50-fold, more preferably at least 75-fold. As described herein before, the average level of CD4$^+$GPA33$^{high}$ Tregs in human peripheral blood is approximately 1-4% of total CD4$^+$ T cells. Methods for enrichment according to the invention preferably result in and isolated population of regulatory T cells wherein at least 75%, more preferably 80%, more preferably 85%, more preferably 90% of the cells are regulatory T cells expressing high GPA33 as described herein above.

Said population of cells preferably comprises mammalian blood cells, synovial fluid cells or lymph cells or comprises cells obtained from mammalian blood, synovial fluid or lymph, wherein said blood is preferably cord blood or peripheral blood.

In a preferred embodiment, a method for enriching a population of cells for regulatory T cells further comprises isolating the CD4$^+$GPA33$^{high}$ T cells. Also provided is an enriched population of regulatory T cells isolated or obtained by the method described above.

An isolated population of cells wherein at least 75% of the cells are CD4$^+$GPA33$^{high}$ regulatory T cells is for instance a population of stable Tregs that has been obtained following isolation from a sample as defined herein or following enrichment for Tregs according to the invention. However, a method for enriching a population of cells for regulatory T cells or a method for isolating regulatory T cells according to the invention may further comprise culturing isolated cells in the presence of one or more factors promoting proliferation, activation and/or growth of said cells, such as crosslinked antibodies to CD3 and CD28 and IL-2. Such culturing preferably results in expansion of said Tregs. This way a sufficient amount of Tregs for administration and/or treatment, alleviation or prevention as described herein can be obtained. Hence, a population of cells may also be a population of stable Tregs that has been obtained following isolation from a sample as defined herein or following enrichment for Tregs according to the invention and subsequent culturing as described herein. Optionally, following said culturing in the presence of said one or more factors promoting proliferation, activation and/or growth of the stable Tregs, the steps of a method for enriching a population of Tregs according to the invention or the steps of a method for isolating Tregs according to the invention are repeated in order to remove any remaining and/or expanded CD4$^+$GPA33$^{low}$ or CD4$^+$GPA33$^-$ T cells prior to administration. For instance, cells are analyzed and/or enriched for CD4$^+$ and GPA33$^{high}$ expression, and optionally CD25$^+$ and CD127$^-$ or CD127$^{low}$ expression, following isolation of cells from e.g. mammalian blood, synovial fluid or lymph; subsequently cultured in the presence of one or more factors promoting proliferation, activation and/or growth of the cells; and analyzed and/or enriched for CD4$^+$ and GPA33$^{high}$ expression, and optionally CD25+ and CD127– or CD127$^{low}$ expression again prior to administration to a patient. As another example, cells are depleted for cells other than CD4$^+$ T cells, such as for cells expression CD8, CD11b, CD11c, CD14, CD16 and CD19 and analyzed and/or enriched for GPA33$^{high}$ expression following isolation of cells from e.g. mammalian blood, synovial fluid or lymph; subsequently cultured in the presence of one or more factors promoting proliferation, activation and/or growth of the cells; and analyzed and/or enriched for CD4$^+$ and GPA33$^{high}$ expression, and optionally CD25$^+$ and CD127$^-$ or CD127$^{low}$ expression prior to administration to a patient. Said one or more factors promoting proliferation, activation and/or growth of the cells are preferably selected from the group consisting of crosslinked antibodies to CD3, crosslinked antibodies to CD28 and IL-2, or combinations thereof.

As used herein, the term "cell sample" refers to tissues or body fluids removed from a mammal, preferably a human, comprising cells. The sample preferably comprises T cells, preferably CD4$^+$ T cells. Preferred samples are a blood sample, a lymph sample, a synovial fluid sample or a tissue sample such as a thymus, spleen, lymph nodes, bone marrow or Peyer's patches sample. A preferred sample is a blood sample or a blood fraction sample comprising cells, a lymph sample or a synovial fluid. A preferred blood or blood fraction sample is or is obtained from peripheral blood or cord blood. Hence, in a preferred embodiment, the sample comprises mammalian blood or T cells obtained from mammalian blood, lymph sample or synovial fluid, wherein said blood is preferably umbilical cord blood or peripheral blood. Methods for obtaining such samples are well known in the art of immunology and surgery and include sampling blood and obtaining biopsies from the relevant tissue or organ. In some embodiment, the sample comprising cells or population of cells used in a method of the invention is obtained from a subject in need of treatment, in particular immunosuppressive treatment.

In other embodiments, sample comprising cells or the population of cells is obtained from a donor distinct from the subject in need of treatment.

Isolation of Tregs and enrichment of a population of cells for Tregs in accordance with the invention, in addition to CD4$^+$ and GPA33$^{high}$ expression, are preferably further based on CD25$^+$ expression and/or CD127$^{low}$ or CD127$^-$ expression, and optionally on the absence of CD8 expression.

Isolation of Tregs and enrichment of a population of cells for Tregs in accordance with the invention are preferably performed using an agent capable of binding CD4 and an agent capable of binding GPA33. In addition, if isolation and enrichment is further based on absence of CD8 expression, expression of CD25 and/or absence or low level of expression of CD127, an agent capable of binding CD8, CD25 and/or CD127 can be used. Said agents preferably specifically bind their target, i.e. CD4, GPA33, CD8, CD25 or CD127.

In a preferred embodiment is provided a method for enriching a population of cells for regulatory T cells comprising:
  a. contacting a population of cells with an agent capable of binding CD4, an agent capable of binding CD25, an agent capable of binding CD127 and an agent capable of binding GPA33,
  b. determining binding of said cells to said agents capable of binding CD4, CD25, CD127 and GPA33, and
  c. selecting and/or isolating cells that do not bind to the agent capable of binding CD127 or bind the said agent at a low level, and that bind to the agents capable of binding CD4, CD25 and GPA33.

Said agents capable of binding CD4 and GPA33, and optionally other markers such as CD25 and CD127, are preferably antibodies or antigen-binding fragments thereof that specifically bind the markers. Hence, an agent capable of binding CD4 is preferably an antibody that specifically binds CD4 or an antigen-binding fragment thereof that specifically binds CD4. An agent capable of binding GPA33 is preferably an antibody that specifically binds GPA33 or an antigen-binding fragment thereof that specifically binds GPA33. An agent capable of binding CD25 is preferably an antibody that specifically binds CD25 or an antigen-binding fragment thereof that specifically binds CD25. An agent capable of binding CD127 is preferably an antibody that specifically binds CD127 or an antigen-binding fragment thereof that specifically binds CD127.

In addition to agents that specifically bind to GPA33, CD4, CD25 and/or CD127, agents that specifically bind other cell surface markers can be used in the methods of the invention to select for or exclude different cell types. Examples of such agents are agent, e.g. antibodies or fragments thereof that specifically bind CD3, CD8, CD45RA, CD19, CD45, etc. In addition ligands or fragments thereof or fusion proteins that comprise such ligand or a fragment thereof that specifically bind GPA33 can be used.

As used herein an antigen-binding fragment of an antibody that specifically binds a cell surface marker, e.g. GPA33, refers to a part of an antibody that has at least one same property as said antibody in that it specifically binds to the same cell surface marker as said antibody and as a result can be used in the detection of the cell surface marker. A fragment preferably comprises at least one or more heavy chain and/or light chain CDR sequences of an antibody that specifically binds to a specific cell surface marker. More preferably, a fragment comprises at the heavy chain CDR1, CDR2 and CDR3 and the light chain CDR1, CDR2 and CDR3 of such antibody, even more preferably the heavy chain variable region and the light chain variable region.

As used herein the term "specifically binds", "specific for" or "capable of specifically binding" refer to the non-covalent interaction between an antibody and its epitope. It indicates that the antibody or fragment thereof preferentially binds to said epitope over other antigens or antigenic determinants. Hence, although the antibody or fragment may non-specifically bind to antigens or antigenic determinants, the binding affinity of said antibody or fragment for its epitope is significantly higher than the binding affinity of said antibody or fragment for any other antigen or antigenic determinant.

Methods for isolating regulatory T cells or for enriching a population of cells for regulatory T cells may further comprise separating the cells that bind to the antibody or antigen-binding fragment thereof or to the antibodies or fragments thereof from the sample to produce an isolated population of $CD4^+GPA33^{high}$ regulatory T cells.

Agents, preferably antibodies or antigen-binding fragment thereof that specifically bind a cell surface marker, are preferably labelled to enable detection and/or isolation of cells expressing the cell surface markers, e.g. by cell sorting. Alternatively, the agents, preferably antibodies or fragments thereof, are targeted with a secondary antibody that is labelled. The antibodies or fragments are for instance conjugated to a fluorochrome and/or to a magnetic or paramagnetic particle. Methods for sorting cells are well known in the art. Cell sorters can be used to separate a mixture of cells into populations of a single cell type. As used herein, the term "sorting" refers to a method by which cells, such as $CD4^+GPA33^{high}$ Tregs of the invention, are sorted based on their optical and/or volumetric properties, such as their shape or fluorescent labelling. In one embodiment, selecting or an isolation step is performed by flow cytometry, fluorescence activated cell sorting (FACS), magnetic selection, magnetic-activated cell sorting (MACS), affinity chromatography or panning, or combinations thereof.

For instance, antibodies or fragments can be conjugated with magnetic beads to allow for separation of Treg cells. Alternatively, the antibodies or fragments can be conjugated to biotin, which binds with high affinity to avidin or streptavidin. As yet another examples, the antibodies or fragments can be conjugated to fluorochromes, which can be used for isolation by flow cytometry, such as by FACS. As indicated herein above, selection for absence or presence of multiple markers can be performed sequentially. Alternatively selection for absence or presence of more than one cell surface marker can be performed at the same time. For instance, multicolour analyses and cell sorting can be performed with FACS. Separation and isolation of cells based on multiple cell surface markers, e.g. CD4, CD25, CD127 and GPA33, can be performed in a single step.

FACS allows for the separation of populations of cells on the basis of light scatter properties thereof when they pass through a laser beam. The forward light scatter is related to cell size, and the side scatter characteristic (SSC) is related to the complexity of the internal structure of a cell. Cells are further characterized by fluorescence intensity after labelling with fluorochrome-conjugated antibodies. Fluorochromes that can be conjugated to antibodies and can be used for isolation of cells, e.g. by cell sorting and/or FACS are well known in the art. Examples of suitable fluorochromes include, but are not limited to, fluorescein isothiocyanate (FITC), phycoerythrin (PE), propidium iodide (PI), Alexa Fluor 488, carboxyfluorescein succinimidyl ester (CFSE), carboxyfluorescein diacetate succinimidyl ester (CFDA-SE), DyLight 488, peridinin chlorophyll protein complex (PerCP), PerCP-Cy5.5, PE-Alexa Fluor 700, PE-Cy5, PE-Alexa Fluor 750, PE-Cy7, allophycocyanin (APC), APC-Cy7, Alexa Fluor 700, Cy5, Pacific Orange, Pacific Blue, Amine Aqua, Pacific Blue, 4',6-diamidino-2-phenylindole HCl (DAPI), Alexa Fluor 405.

Magnetic separation is based on selective retention of magnetically labelled cells within e.g. a tube or column in a magnetic field gradient. Tregs can be magnetically labelled by binding magnetic particles to the surface of the cells through specific interactions, such as by labelling the cells with antibodies conjugated to magnetic particles. Examples of suitable magnetic particles that can be used to select and/or isolate cells, such as the $GPA33^+$ Tregs of the invention, include, but are not limited to, MACS particles (Miltenyi Biotec), StemSep™ colloid (StemCell Technologies), EasySep (StemCell Technologies), Imag particles (BD Biosciences), Dynabeads (Dynal Biotech).

The invention also provides a method for identifying regulatory T cells comprising analyzing $CD4^+$ T cells for expression of GPA33, wherein a $CD4^+GPA33^{high}$ expression pattern is indicative of a regulatory T cell or a population of regulatory T cells. In one embodiment, said method comprises analyzing cells for expression of CD4 and GPA33, wherein a $CD4^+GPA33^{high}$ expression pattern is indicative of a regulatory T cell or a population of regulatory T cells. Said regulatory T cells are preferably stable regulatory T cells. It further is preferred that the cells that are isolated are $CD4^+CD25^+CD127^-GPA33^{high}$ or $CD4^+CD25^+CD127^{low}GPA33^{high}$ cells. Also provided is a method for detecting regulatory T cells comprising analyzing cells for expression of CD4 and GPA33, wherein a $CD4^+GPA33^+$ expression pattern is indicative of a regulatory T cell or a population of regulatory T cells. Said regulatory T cells that are detected are in particular stable regulatory T cells, whereby a $CD4^+GPA33^{high}$ expression pattern is indicative of a regulatory T cell or a population of regulatory T cells. It further is preferred that the cells are further analyzed for expression of CD25 and CD127, whereby $CD4^+CD25^+CD127^-GPA33^{high}$ or $CD4^+CD25^+CD127^{low}GPA33^{high}$ expression pattern is indicative of a regulatory T cell or a population of regulatory T cells. Also provided is a method for detecting regulatory T cells in a sample, said method comprising detecting whether $CD4^+GPA33^{high}$ cells are present in the sample by contacting the sample with an anti-GPA33 antibody or antigen-binding fragment thereof and an anti-CD4 antibody or antigen-binding fragment thereof and detecting binding between GPA33 and the anti-GPA33 antibody or fragment and between CD4 and the anti-CD4 antibody or fragment. It further is preferred that the cells are further analyzed for expression of CD25 and CD127. Hence, it is preferred that the method comprises detecting whether $CD4^+CD25^+CD127^-GPA33^{high}$ or $CD4^+$ CD25$^+$CD127$^{low}$GPA33$^{high}$ cells are present in the sample by further contacting the sample with an anti-CD25 antibody or antigen-binding fragment thereof and an anti-CD127 antibody or antigen-binding fragment thereof and detecting binding between CD25 and the anti-CD25 antibody or fragment and between CD127 and the anti-CD127 antibody or fragment.

Said methods preferably comprise detection of the presence or absence and/or the level of expression of GPA33 on the surface of said cells that are analyzed using an agent capable of specifically binding GPA33, detection of the presence or absence of CD4 on the surface of said cells that are analyzed using an agent capable of specifically binding CD4, detection of the presence or absence of CD25 on the surface of said cells that are analyzed using an agent capable of specifically binding CD25 and/or detection of the presence or absence or expression level of CD127 on the surface of said cells that are analyzed using an agent capable of specifically binding CD127. It is preferred that at least CD4 and GPA33 expression on the surface of said cells that are analyzed is detected. In a further preferred embodiment, at least CD4, CD25, CD127 and GPA33 expression on the surface of said cells that are analyzed is detected. As described herein before for isolation of Tregs, expression of these markers can be detected sequentially, in any order, simultaneously, or a combination thereof.

The invention further provides GPA33 as a marker for Tregs, preferably as a marker for stable Tregs or tTregs. In a preferred embodiment, GPA33 is used in combination with CD4 as a marker for Tregs. In another preferred embodiment GPA33 is used in combination with CD4, CD25 and CD127 as a marker for Tregs, preferably as a marker for stable Tregs or tTregs.

CD4$^+$GPA33$^{high}$ cells, preferably CD4$^+$CD25$^+$CD127$^-$GPA33$^{high}$ or CD4$^+$CD25$^+$CD127$^{low}$GPA33$^{high}$ cells a population of Tregs according to the invention or a population isolated or obtained with a method according to the invention can be advantageously used in therapeutic applications. Provided is therefore a pharmaceutical composition comprising CD4$^+$GPA33$^{high}$ T cells, preferably CD4$^+$CD25$^+$CD127$^-$GPA33$^{high}$ or CD4$^+$CD25$^+$CD127$^{low}$GPA33$^{high}$ cells, or comprising a population of cells according to the invention and a pharmaceutically acceptable carrier, diluent and/or excipient.

By "pharmaceutically acceptable" it is meant that the carrier, diluent or excipient must be compatible with the other ingredients of the formulation and not deleterious to the recipient thereof. In general, any pharmaceutically suitable additive which does not interfere with the function of the active compounds can be used. A pharmaceutical composition according to the invention is preferably suitable for human use. Examples of suitable carriers comprise a solution, lactose, starch, cellulose derivatives and the like, or mixtures thereof. In a preferred embodiment said suitable carrier is a solution, for example saline. For making dosage units, e.g. tablets, the use of conventional additives such as fillers, colorants, polymeric binders and the like, is contemplated. Examples of excipients which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor. Compositions for intravenous administration may for example be solutions of the compounds of the invention in sterile isotonic aqueous buffer. Where necessary, the intravenous compositions may include for instance solubilizing agents, stabilizing agents and/or a local anesthetic to ease the pain at the site of the injection.

In an embodiment of the invention, a pharmaceutical kit or kit of parts is provided comprising one or more containers filled with one or more pharmaceutical compositions according to the invention and optionally one or more pharmaceutically acceptable carriers, diluents and/or excipients as described herein. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration. Preferably, a pharmaceutical kit or kit of parts comprises instructions for use.

Also provided are CD4$^+$GPA33$^{high}$ T cells, preferably CD4$^+$CD25$^+$CD127$^-$GPA33$^{high}$ or CD4$^+$CD25$^+$CD127$^{low}$GPA33$^{high}$ cells, or a population of cells according to the invention for use in therapy.

Further provided are CD4$^+$GPA33$^{high}$ T cells, preferably CD4$^+$CD25$^+$CD127$^-$GPA33$^{high}$ or CD4$^+$CD25$^+$CD127$^{low}$GPA33$^{high}$ cells, or a population of cells according to the invention for use in suppressing an immune response. Also provided is a method for suppressing an immune response in a subject in need thereof comprising administering to the subject a therapeutically effective amount of CD4$^+$GPA33$^{high}$ T cells, preferably CD4$^+$CD25$^+$CD127$^-$GPA33$^{high}$ or CD4$^+$CD25$^+$CD127$^{low}$GPA33$^{high}$ cells, or a population of cells according to the invention. Also provided is a use of CD4$^+$GPA33$^{high}$ T cells, preferably CD4$^+$CD25$^+$CD127$^-$GPA33$^{high}$ or CD4$^+$CD25$^+$CD127$^{low}$GPA33$^{high}$ cells, or a population of cells according to the invention for the preparation of a medicament for suppressing an immune response in a subject in need thereof. As used herein the term "suppressing an immune response" refers to the reduction, weakening or prevention of an immune response in a subject. For instance, the subject's immune system is prevented from mounting an immune response, e.g. after an organ or tissue transplant, an immune response already initiated in a subject is reduced, e.g. in response to a disease that is caused by an overactive immune system such as an autoimmune disease or a chronic inflammatory disease. Suppressing an immune response is preferably for the treatment, alleviation or prevention of graft versus host disease (GVHD), for the treatment, alleviation or prevention of transplant rejection or for the treatment, alleviation or prevention of a chronic inflammatory condition or an autoimmune disease.

The invention further provides CD4$^+$GPA33$^{high}$ T cells, preferably CD4$^+$CD25$^+$CD127$^-$GPA33$^{high}$ or CD4$^+$CD25$^+$CD127$^{low}$GPA33$^{high}$ cells, or a population of cells according to the invention for use in the treatment, alleviation or prevention of graft versus host disease (GVHD), transplant rejection, a chronic inflammatory condition or an autoimmune disease. Also provided is a method for treatment, alleviation or prevention of graft versus host disease (GVHD), transplant rejection, a chronic inflammatory condition or an autoimmune disease, the method comprising administering to a subject in need thereof CD4$^+$GPA33$^{high}$ T cells, preferably CD4$^+$CD25$^+$CD127$^-$GPA33$^{high}$ or CD4$^+$CD25$^+$CD127$^{low}$GPA33$^{high}$ cells, or a population of cells according to the invention. Also provided is a use of CD4$^+$GPA33$^{high}$ T cells, preferably CD4$^+$CD25$^+$CD127$^-$GPA33$^{high}$ or CD4$^+$CD25$^+$CD127$^{low}$GPA33$^{high}$ cells, or a population of cells according to the invention for the preparation of a medicament for the treatment, alleviation or prevention of graft versus host disease (GVHD), transplant rejection, a chronic inflammatory condition or an autoimmune disease.

Examples of a condition or disease that can be treated, alleviated and/or prevented with a method of the invention include, but are not limited to, a condition or disease selected from the group consisting of type 1 diabetes, multiple sclerosis (MS), systemic lupus erythematosus (SLE), rheumatoid arthritis, psoriatic arthritis, osteoarthritis, ankylosing spondylitis, aplastic anemia, thrombocytopenia purpura, Graves disease, Addison's disease, psoriasis, uveitis, autoimmune hemolytic anemia, inflammatory bowel disease, ulcerative colitis, Crohn's disease, an allergic condition and an asthmatic condition.

The term "therapeutically effective amount" as used herein refers to the amount of the pharmaceutical composition, which provides a therapeutic benefit in the prevention, treatment, or management, of the disease being treated. As used herein, the terms "subject" and "individual" encompasses humans and animals, preferably mammals. Preferably, a subject or individual is a mammal, more preferably a human.

As used herein, the term "prevention" refers to preventing or delaying the onset of a condition or disease and/or the appearance of clinical symptoms of the condition or disease in a subject that does not yet experience clinical symptoms of the disorder or disease. The term "treatment" refers to inhibiting the disorder or disease, i.e., halting or reducing its development or at least one clinical symptom thereof, and to relieving symptoms of the disorder or disease. A population of Tregs according to the invention or a population of Tregs prepared or enriched with a method of the invention are particularly useful in adoptive immunotherapy or adoptive regulatory T cell transfer. As used herein, the term "adoptive immunotherapy" refers to the transfer of cells into a patient. Similarly, "adoptive regulatory T cell transfer" refers to the transfer of cells into a patient. The cells may have originated from the patient itself (autologous adoptive cell transfer or immunotherapy) or may have come from a donor other than the patient itself (allogenic adoptive cell transfer or immunotherapy).

GPA33 is further particularly suitable for use as a marker for autoimmune diseases. Many autoimmune diseases are at least in part attributable to Treg insufficiency. Examples of such diseases are systemic lupus erythematosus (SLE) and rheumatoid arthritis (RA). In the Examples (see FIG. 12) it is shown that GPA33 levels can change dramatically in different autoimmune diseases that are associated with Treg insufficiency. FIG. 12 shows that the levels of GPA33 expression in different autoimmune diseases is reduced as compared to the levels of GPA33 expression in healthy individuals. In particular, it is shown that patients having a hereditary mutation in the CTLA-4 gene, which results in reduced Treg functionality, have a reduced GPA33 expression level in blood. Further, patients suffering from APECED (autoimmune polyendocrinopathy-candidiasis-ectodermal dystrophy) also have reduced levels of GPA33 expression in blood cells. APECED is characterized by a mutation in the Aire gene, as a result of which a subset of self reactive Tregs is not generated in the thymus leading to multi-organ inflammation due to a lack of tolerance induced against a subset of antigens. In a third patient, in which the specific autoimmune disorder is unknown, the GPA33 expression pattern differs from that in the other two autoimmune disease patients, and the GPA33 expression pattern more closely resembles that in healthy controls. These results show that GPA33 is differentially expressed in some but not all autoimmune disorders. Hence, expression level of GPA33 can be used as a marker in autoimmune disease, in particular to determine whether or not a particular autoimmune disease is associated with Treg insufficiency. For instance, such method allows discriminating between different autoimmune disorders that are symptomatically similar but are distinguishable by the presence or absence of Treg insufficiency. Therefore, in one aspect GPA33$^{high}$ Tregs are detected using a method of the invention in a sample from a patient suffering from an autoimmune disease. Such method can be used in determining from which autoimmune disease the patient is suffering. Hence, in a preferred embodiment, it is unknown from which autoimmune disease the patient is suffering.

The invention therefore provides a method for detecting regulatory T cells in a sample with a method according to the invention, wherein said sample is a sample from an individual suffering from an autoimmune disease. In one aspect, said sample is a sample from an individual suffering from an unidentified autoimmune disease. Said sample preferably comprises blood, synovial fluid or lymph, or comprises T cells obtained from blood, synovial fluid or lymph, wherein said blood is peripheral blood. Said method further preferably comprises quantifying the level of CD4$^+$GPA33$^{high}$ cells in said sample, more preferably quantifying the level of CD4$^+$CD25$^+$GPA33$^{high}$ cells in said sample.

Also provided is a method for classifying an autoimmune disease as an autoimmune disease characterized by regulatory T cell insufficiency, the method comprising quantifying the level of CD4$^+$GPA33$^{high}$ cells in a sample from an individual suffering from an autoimmune disease in accordance with a method and comparing said level with the level of CD4$^+$GPA33$^{high}$ cells in a reference sample. It is preferred that the levels of CD4$^+$CD25$^+$GPA33$^{high}$ cells is quantified and compared with the level of CD4$^+$CD25$^+$GPA33$^{high}$ cells in a reference sample.

As used herein "quantifying the level of CD4$^+$GPA33$^{high}$ cells" and "quantifying the level of CD4$^+$CD25$^+$GPA33$^{high}$ cells" refer to determining the absolute or relative amount of CD4$^+$GPA33$^{high}$ or CD4$^+$CD25$^+$GPA33$^{high}$ cells in the sample so that the sample can be compared with a reference sample, e.g. a sample from a healthy individual. A reference sample as used herein relating to the use of GPA33 in classifying an autoimmune disease preferably is a sample from a healthy individual. As used herein a sample from a healthy individual refers to a sample of an individual that is not suffering from Treg insufficiency. Treg insufficiency refers to a reduction in Treg levels and/or Treg function as compared to the average Treg level and/or Treg function in a population.

GPA33 is further suitable for use as a marker for typing or prognosticating tumors. Despite their phenotypic similarity, CD4$^+$CD25$^+$ Tregs and CD4$^+$CD25$^+$ conventional T cells (in the Examples herein referred to as P3 cells) have dramatically different functional capacities. Whereas eTregs suppress immunity and lack the capacity to make inflammatory cytokines, CD4$^+$CD25$^+$CD45RA conventional T cells make inflammatory cytokines and are not suppressive.

Whereas the presence of bona fide eTregs in tumors is associated with a poor prognosis, the reverse is true for the presence of these CD4$^+$CD25$^+$CD45RA T cells (Saito et al. 2016), which is thought to be associated with the capacity of these cells to produce IFNγ and IL-17. Saito et al. show that both of these two different CD4$^+$ T cells express FoxP3, but the expression pattern is different. eTregs have a high FoxP3 expression whereas the second population is characterized by a lower expression of FoxP3. The CD4$^+$FoxP3$^{low}$ T cells described by Saito et al. are the P3 cells shown in the FIGS. 1 and 3 of this application. Distinction of these cells is difficult, as the CD4$^+$CD25$^+$ Tregs can be either CD45RA$^+$ or CD45RA$^-$ and the CD4$^+$CD25$^+$ non-Tregs can be either CD127$^+$ or CD127$^-$. Further, the differentiation between CD4$^+$FoxP3$^{high}$ T cells and CD4$^+$FoxP3$^{low}$ T cells as described by Saito et al. based on markers currently used (i.e. FoxP3 or CD25) is rather arbitrary, as the difference in these markers is not well defined and gradual rather than discrete.

Indeed, as shown in the current Examples, the CD4$^+$FoxP3$^{low}$ described by Saito et al. can be either GPA33$^+$ or GPA33$^-$ (see FIG. 1, P3 cells). The GPA33$^-$ cells produce IFNγ and IL-17 and are thus the CD4$^+$FoxP3$^+$ T cells that are non-immunosuppressive and associated with a good survival prognosis of tumor patients. The GPA33$^+$ cells are IFNγ and IL-17 negative as shown in FIG. 5 and are the CD4$^+$FoxP3$^+$ T cells that are immunosuppressive cells associated with a poor survival prognosis. Hence, GPA33 is also a better marker as compared to existing T cell markers for determining whether CD4$^+$ T cells in a tumor are associated with a good or poor prognosis.

Hence, the presence of CD4$^+$CD25$^+$GPA33$^+$ Tregs in a tumor is correlated with a poor prognosis while the presence of CD4$^+$CD25$^+$GPA33$^-$ T cells is associated with a good prognosis. With the identification of GPA33 as a marker that is present on Tregs and absent on CD4$^+$CD25$^+$ conventional T cells, it has now become possible to unequivocally distinguish CD4$^+$CD25$^+$ T cells associated with a poor or good prognosis. GPA33 is therefore particularly suitable as a marker in determining the presence and/or absence and level of Tregs and conventional T cells in a tumor which are associated with opposite prognosis in patients suffering from a tumor. GPA33 expression of T cells in a tumor can for instance be assessed as part of determining the immune score in these patients. The immune score, whereby the type and level of immune cells of tumors is determined, has recently gained interest as an approach for the classification of tumors, and can be used inter alia for outcome prediction as part of the diagnostic and prognostic assessment of tumors. In particular, the immune score can be used for determining survival prognosis and response to treatment, in particular response to treatment by immunotherapy. Until recently, tumor classification, for instance of colorectal tumors, has mainly been based on histopathological analysis of tumor tissue following surgical removal. Such classification unfortunately provides limited information for prognosis since cancer outcome can significantly vary among patients within the same histological tumor stage.

Therefore, in one embodiment, a method for detecting GPA33$^{high}$ regulatory T cells according to the invention is provided, wherein the CD4$^+$ T cells analyzed for GPA33 expression are obtained from a tumor or a tumor sample.

Further provided is a method for distinguishing CD4$^+$CD25$^+$ regulatory T cells and CD4$^+$CD25$^+$ conventional T cells, comprising determining in a tumor sample comprising T cells the presence or absence of expression of CD4, CD25 and GPA33 on the surface of said T cells.

Also provided is a use of GPA33 as a marker for prognosis in cancer.

Also provided is a use of GPA33 as a prognostic marker in an individual suffering from cancer.

Also provided is a method for classifying an individual suffering from cancer as having a poor prognosis or a good prognosis, the method comprising:
  a) determining the level of CD4$^+$CD25$^+$GPA33$^{high}$ T cells in a tumor sample
  b) determining the level of CD4$^+$CD25$^+$GPA33$^{high}$ T cells in a reference sample, and
  c) comparing the level of CD4$^+$CD25$^+$GPA33$^{high}$ T cells in said tumor sample determined in a) with the level of CD4$^+$CD25$^+$GPA33$^{high}$ T cells in said reference sample determined in b),
wherein a level of CD4$^+$CD25$^+$GPA33$^{high}$ T cells in said tumor sample that is higher than the level of CD4$^+$CD25$^+$GPA33$^{high}$ T cells in said reference sample is indicative of a poor prognosis. In a further aspect, a good prognosis is predicted if the level of CD4$^+$CD25$^+$GPA33$^{high}$ T cells in said tumor sample is lower than the level of CD4$^+$CD25$^+$GPA33$^{high}$ T cells in said reference sample.

Also provided is a method for typing a tumor sample of an individual suffering from cancer, the method comprising:
  a) determining a level of CD4$^+$CD25$^+$GPA33$^{high}$ T cells in a tumor sample
  b) determining a level of CD4$^+$CD25$^+$GPA33$^{high}$ T cells in a reference sample, and
  c) typing said tumor sample on the basis of the levels of CD4$^+$CD25$^+$GPA33$^{high}$ T cells determined in said tumor sample and said reference sample.

In a further aspect, a good prognosis is predicted if the level of CD4$^+$CD25$^+$GPA33$^{high}$ T cells in said tumor sample is lower than the level of CD4$^+$CD25$^+$GPA33$^{high}$ T cells in said reference sample.

As used herein "classifying an individual suffering from cancer as having a poor prognosis or a good prognosis" refers to predicting whether said individual has a poor or good prognosis. As used herein "prognosis" refers to predicting the progression or outcome of a condition, in particular cancer, in an individual. The term "prognosis" does not refer to predicting the progression or outcome with 100% accuracy or certainty. Instead, it will be understood that the term prognosis refers to an increased probability that a certain progression or outcome occurs. In a preferred embodiment, the term "prognosis" refers to survival prognosis, such as a 1 year or 5 year survival prognosis, i.e. the likelihood that the individual suffering from cancer will survive the indicated period of time.

As described herein, the CD4$^+$GPA33$^{high}$ Tregs suppress immunity and lack the capacity to make inflammatory cytokines. As such, Tregs are potent immunosuppressive cells that promote progression of cancer through their ability to limit antitumor immunity and promote angiogenesis. Hence, also provided is therefore a method for predicting response to therapy in an individual suffering from cancer, the method comprising:
  a) determining a level of CD4$^+$CD25$^+$GPA33$^{high}$ T cells in a tumor sample
  b) determining a level of CD4$^+$CD25$^+$GPA33$^{high}$ T cells in a reference sample, and
  c) comparing the level of CD4$^+$CD25$^+$GPA33$^{high}$ T cells in said tumor sample with the level of CD4$^+$CD25$^+$GPA33$^{high}$ T cells in said reference sample,
wherein a level of CD4$^+$CD25$^+$GPA33$^{high}$ T cells in said tumor sample that is higher than the level of CD4$^+$CD25$^+$GPA33$^{high}$ T cells in said reference sample is indicative of a poor response to therapy. In a further aspect, a good response to therapy is predicted if the level of CD4$^+$CD25$^+$GPA33$^{high}$ T cells in said tumor sample is lower than the level of CD4$^+$CD25$^+$GPA33$^{high}$ T cells in said reference sample.

As used herein "response to therapy" refers to the presence or absence of a clinically significant benefit resulting from therapy and may for instance be evidenced by a clinically relevant parameter, such as tumor shrinkage, reduced tumor growth, inhibition of symptoms and survival. A good response to treatment refers to the presence of such benefit, whereas a poor response to treatment refers to the absence of such benefit. Said therapy can be any type of tumor therapy, including radiation therapy, chemotherapy and immunotherapy. In a preferred embodiment, response to immunotherapy is determined. "Immunotherapy" as used herein refers to treatment of an individual by a method that comprises inducing or enhance an immune response against tumor cells.

The effect of CD4$^+$CD25$^+$GPA33$^+$ Tregs and CD4$^+$CD25$^+$GPA33$^-$ Tconv on prognosis or response to therapy is typically independent of the tumor type. Tregs are found to infiltrate tumors in a vast array of tumor types, and these tumor-infiltrating Tregs are associated in many of these tumor types with a poor clinical outcome. Non-limiting examples of cancers in which GPA33 can be used as a prognosis marker are lung cancer, colorectal cancer, breast cancer, prostate cancer, pancreatic cancer, ovarian cancer brain cancer, bladder cancer, cervical cancer, liver cancer, kidney cancer, leukemia, melanoma, neuroblastoma, renal cancer, skin cancer, sarcoma, uterine cancer, carcinomas of the esophagus and gastrointestinal tract or a hematologic malignancy such as multiple myeloma, B-cell lymphoma, T-cell lymphoma, non-Hodgkin's lymphoma and Hodgkin's lymphoma. In a preferred embodiment, said cancer is colorectal cancer and/or said individual is suffering from colorectal cancer, more preferably colon carcinoma. A cancer that originates in the colon or rectum is termed a colorectal cancer or bowel cancer. Said cancer comprises colon cancer and rectal cancer. In a preferred embodiment, a colorectal cancer as used herein relates to a colon cancer, more preferably colon carcinoma. In another preferred embodiment, a colorectal cancer according to the invention relates to a rectal cancer.

As used herein a "tumor sample" refers to a sample comprising tumor cells. Such tumor sample is obtained from a patient suffering from said tumor and can either be directly used for analysis or following storage for instance at 4° C., −20° C. or −70° C. Tumor samples and reference samples can be obtained using any method known in the art. For instance, the samples can be obtained during surgery, e.g. during surgery aimed at removal of a tumor, or the samples are obtained from one or more biopsies. For instance, if the cancer is colorectal cancer, a tumor sample and a reference are obtained directly from the large intestine during surgery. In an alternative embodiment, the samples are prepared from biopsy samples that are taken during colonoscopy.

The reference sample relating to the use of GPA33 as a marker and/or in typing or prognosticating tumors and/or predicting response to therapy in an individual suffering from cancer is preferably a sample of healthy tissue of the same type as the tissue in which the tumor has developed, for instance healthy tissue surrounding the tumor or healthy tissue that is more distant from the tumor but of the same type. For instance, if the cancer is colorectal cancer, the reference sample is a sample of healthy colorectal tissue, such as colonic tissue. Hence, in a preferred embodiment, a reference sample is a sample from said individual of healthy tissue surrounding said tumor or a sample of healthy tissue of the same type of tissue as the tissue containing said tumor. In a further preferred embodiment, the cancer is colorectal cancer, more preferably colon carcinoma, and the reference sample is a sample of healthy colorectal tissue, such as colonic tissue.

In a preferred embodiment, the tumor and reference sample comprise isolated cells, preferably viable cells, or one or more tissue sections, such as paraffin sections or frozen sections. CD4$^+$CD25$^+$GPA33$^{high}$ T cells can for instance be detected and quantified in isolated cells or tissue sections using antibodies specific for CD4 and antibodies specific for GPA33 as described herein.

As used herein, "individual" is preferably a human individual.

Determining the level of CD4$^+$CD25$^+$GPA33$^{high}$ T cells preferably comprises quantifying CD4$^+$CD25$^+$GPA33$^{high}$ T cells, more preferably quantifying the amount of CD4$^+$CD25$^+$GPA33$^{high}$ T cells. Alternatively, the ratio or percentage of CD4$^+$CD25$^+$GPA33$^{high}$ T cells is determined. For instance a ratio of CD4$^+$CD25$^+$GPA33$^{high}$ T cells to CD4$^+$CD25$^+$GPA33$^{intermediate}$ and CD4$^+$CD25$^+$GPA33$^{low}$ T cells in the tumor and reference sample or the percentage of CD4$^+$CD25$^+$GPA33$^{high}$ T cells in the total population of CD4$^+$ T cells in the tumor and reference sample is determined. Preferably, the percentage of CD4$^+$CD25$^+$GPA33$^{high}$ T cells on total CD4$^+$ T cells is determined.

The ratio of CD4$^+$CD25$^+$GPA33$^{high}$ T cells to CD4$^+$CD25$^+$GPA33$^{intermediate}$ and CD4$^+$GPA33$^{low}$ T cells is for instance determined as follows:

$$\text{ratio} = CD4^+CD25^+GPA33^{high} \text{ T cells}: (CD4^+CD25^+GPA33^{intermediate} + CD4^+CD25^+GPA33^{low} \text{ T cells}).$$

The percentage of CD4$^+$CD25$^+$GPA33$^{high}$ T cells in the total population of CD4$^+$ T cells is for instance determined as follows:

$$\text{percentage of } CD4^+CD25^+GPA33^{high} \text{ T cells} = (CD4^+CD25^+GPA33^{high} \text{ T cells}/CD4^+ \text{ T cells})*100.$$

The level, ratio or percentage determined in the tumor sample and reference sample can be determined in any order. I.e. either first the ratio or percentage in the tumor sample is determined and subsequently the ratio or percentage in the reference sample is determined or first the ratio or percentage in the reference sample is determined and subsequently the ratio or percentage in the tumor sample.

As described herein, a level, ratio or percentage of CD4$^+$CD25$^+$GPA33$^{high}$ T cells in the tumor sample that is higher than the level of CD4$^+$CD25$^+$GPA33$^{high}$ T cells in the reference sample is indicative of a poor prognosis. A particularly suitable threshold to classify an individual suffering from cancer as having a poor prognosis is the mean of the level, ratio or percentage of CD4$^+$CD25$^+$GPA33$^{high}$ T cells in the reference sample plus twice the standard deviation. Hence, in a preferred embodiment, a level, ratio or percentage as described herein in the tumor sample that is higher than the mean+(2×standard deviation) of the level, ratio or percentage in the reference sample is indicative of a poor prognosis. For this purpose the average and standard deviation of multiple measurements of CD4$^+$CD25$^+$GPA33$^{high}$ T cells in a reference sample are determined, for instance, three, four, five, six or more measurements in a single or multiple reference samples. Further, the mean of the level, ratio or percentage as described herein in a single or multiple tumor sample can be determined, for instance three, four, five, six or more measurements in a single or multiple tumor samples.

In a further aspect, a good prognosis is predicted if the level of CD4$^+$CD25$^+$GPA33$^{high}$ T cells in said tumor sample is lower than the mean minus twice the standard deviation of the level of CD4$^+$CD25$^+$GPA33$^{high}$ T cells in said reference sample. In a further aspect, a good response to therapy is predicted if the level of CD4$^+$CD25$^+$GPA33$^{high}$ T cells in said tumor sample is lower than the mean minus twice the standard deviation of the level of CD4$^+$CD25$^+$GPA33$^{high}$ T cells in said reference sample.

Determining the level, amount, ratio or percentage of CD4$^+$CD25$^+$GPA33$^{high}$ T cells as described herein, is preferably performed on cells in the tumor and reference samples. For instance, CD4$^+$CD25$^+$GPA33$^{high}$ T cells can be quantified on isolated cells. Hence, in a preferred embodiment, the tumor and reference sample comprise isolated cells, preferably viable cells. CD4$^+$CD25$^+$GPA33$^{high}$ T cells can for instance be detected and quantified with (e.g. fluorescently labelled) antibodies specific for CD4 and antibodies specific for GPA33 using flow cytometry as described herein. Alternatively, CD4$^+$CD25$^+$GPA33$^{high}$ T cells can be quantified in tissue section, such as paraffin sections or frozen sections. CD4$^+$CD25$^+$GPA33$^{high}$ T cells can then for instance be detected and quantified with antibodies specific for CD4, antibodies specific for CD25 and antibodies specific for GPA33, which antibodies can either be (e.g. fluorescently) labelled or be incubated with a secondary antibody, followed by staining and quantification using microscopy. Labels and methods for staining and detecting antibodies using flow cytometry are well known to the skilled person. Quantification of cells stained with antibodies in tissue sections are also well known in the art. Quantification can for instance be performed using microscopy, optionally fluorescent microscopy. In addition to detection of CD4 and GPA33, other T cell marker as described herein can be detected in the methods and uses of the invention, such as CD25, CD127 and/or CD45RA, for instance using antibodies specific for these T cell markers.

In one preferred embodiment a method is provided for classifying an individual suffering from colorectal cancer as having a poor prognosis or a good prognosis, the method comprising:
  a) providing one or more colorectal tumor samples and one or more samples of healthy colonic tissue from said individual,
  b) determining a percentage of CD4$^+$CD25$^+$GPA33$^{high}$ T cells in the total population of CD4$^+$ T cells in said one or more tumor sample,
  c) determining a percentage of CD4$^+$CD25$^+$GPA33$^{high}$ T cells in the total population of CD4$^+$ T cells in said one or more samples of healthy colonic tissue, and
  d) comparing said percentage of CD4$^+$CD25$^+$GPA33$^{high}$ T cells in said one or more tumor samples and said percentage of CD4$^+$CD25$^+$GPA33$^{high}$ T cells in said one or more samples of healthy colonic tissue,
wherein said one or more samples comprise isolated cells or one or more tissue sections, and
  wherein a percentage of CD4$^+$CD25$^+$GPA33$^{high}$ T cells in said one or more tumor samples that is higher than the mean+(2×standard deviation) of the percentage of CD4$^+$CD25$^+$GPA33$^{high}$ T cells in said one or more samples of healthy colonic tissue is indicative of a poor prognosis.

In yet another aspect, the invention provides a method of assigning treatment to an individual suffering from cancer, preferably colorectal cancer, comprising predicting response to treatment by immunotherapy in an individual suffering from cancer in accordance with a method of the invention, and assigning immunotherapy if a good response to treatment is predicted.

Features may be described herein as part of the same or separate aspects or embodiments of the present invention for the purpose of clarity and a concise description. It will be appreciated by the skilled person that the scope of the invention may include embodiments having combinations of all or some of the features described herein as part of the same or separate embodiments.

The invention will be explained in more detail in the following, non-limiting examples.

EXAMPLES

Materials and Methods

Cell Isolation and Cell Sorting

Figure 1:
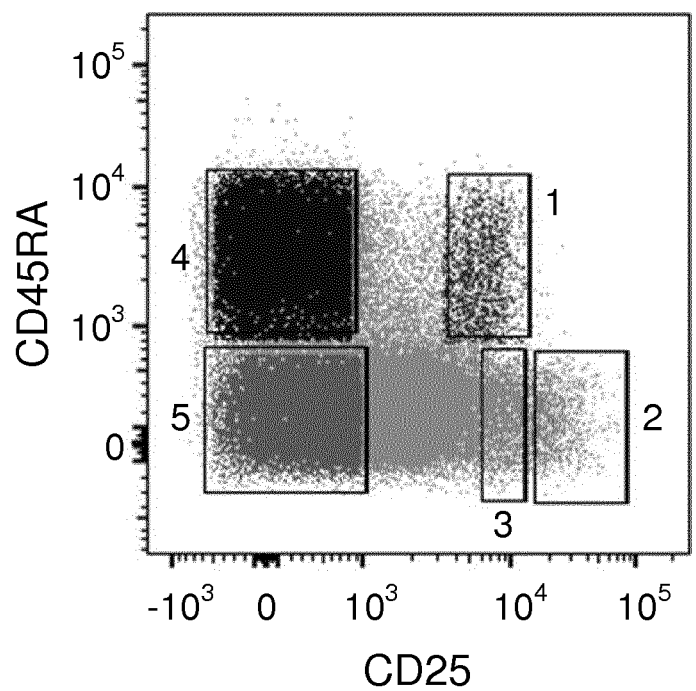
FIG. 1: Five CD4 T cell populations from human blood. Human peripheral blood CD4$^+$ T cells were isolated from healthy donors and analyzed for expression of CD45RA and CD25 (top) as well as for FoxP3 and Helios in each of the five populations (bottom-colors and numbers match those in top figure).
Figure 1:
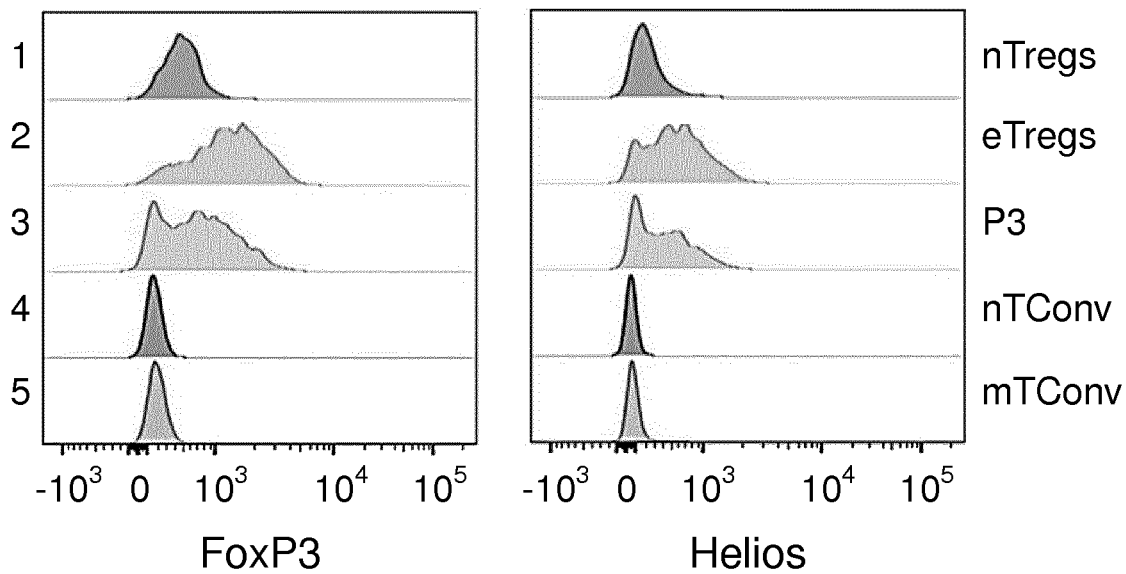

Human peripheral blood mononuclear cells (PBMCs) were obtained from fresh buffy coats from healthy male donors using Ficoll-Paque Plus (GE Healthcare) gradient centrifugation. Total CD4$^+$ T cells were isolated using magnetic sorting with CD4 microbeads (Miltenyi Biotec) and then viable cells were separated using flow-cytometric sorting for CD25 (43839, BD), CD127 (351309, Biolegend) and CD45RA (560675, BD) on a FACS Aria III (BD Biosciences). Blood samples were obtained from anonymized volunteers with written informed consent used in accordance to guidelines established by the Medical Ethical Committee.

Flow Cytometry

Cells were labeled with fluorochrome-conjugated antibodies in PBS 0.5% BSA for 30 min at 4° C. For intracellular and nuclear staining, cells were fixed and permeabilized using Foxp3/Transcription Factor Fixation/Permeabilization buffers (eBioscience) according to the manufacturer's instructions. Cells were analyzed on LSR Fortessa or LSR II cytometers (BD Biosciences). Antibodies against the following molecules were used: CD25, CD45RA, CD127, FOXP3 (25-4777-42, eBioscience), Helios (48-9883, eBioscience). The antibody against GPA33 [Heath, J. K., et al. 1997], a gift from Dr. A. Scott (Olivia Newton-John Cancer Research Institute, Heidelberg Australia) was labeled with APC using the Lynx rapid APC antibody conjugation kit (LNK032APC, Biorad).

Quantification of Proteins by Mass Spectrometry.

FACS-purified CD4$^+$ subsets were washed in PBS and immediately lysed in lysis buffer (4% SDS, 100 mM DTT, 100 mM Tris HCl [pH 8.0]) in Protein LoBind tubes (Eppendorf). The samples were then boiled, sonicated (Bioruptor), and after centrifugation (16,000 g), the supernatants were kept frozen at −80° C. Cell lysates were then processed using filter aided sample preparation (FASP). Briefly, lysates were subjected to reduction, alkylation and insolution digestion with sequencing-grade trypsin (Promega). After digestion, peptides were desalted using StageTips, reduced in a speedvac, and reconstituted in 2% acetonitrile in 0.1% TFA in water before analysis by MS. MS experiments were performed in triplicate by nanoscale C18 reverse phase chromatography coupled online to an Orbitrap Fusion Tribrid mass spectrometer (Thermo Scientific) via a nanoelectrospray ion source (Nanospray Flex Ion Source, Thermo Scientific). Tandem mass spectrometry was performed by isolation using the quadrupole with isolation window 1.6, high collision dissociation (HCD) fragmentation, and rapid scan mass spectrometry analysis in the ion trap.

All data were acquired with Proteome Discoverer software (version 2.0, Thermo Scientific) and RAW mass spectrometry files were processed with the MaxQuant computational platform version 1.5.3.30 using the label-free quantitation (LFQ) algorithms [Cox, J. and M. Mann 2008]. Peptides were identified using the Andromeda search engine by querying the human Uniprot database with a 1% false discovery rate (FDR) cut-off both at peptide and protein level. Potential contaminants and reverse hits were eliminated using Perseus version 1.5.0.31. Absolute protein abundance was estimated using the proteomic ruler methodology using a plug-in built in Perseus as described by the authors [Wisniewski, J. R., et al. 2014]. The abundances were expressed as protein copy numbers and the values were log 10 transformed and presented in graphs using Prism 6.0 (GraphPad Software, San Diego, CA, USA).

RNA Isolation

Total RNA was extracted from $1\times10^6$ cells using TRIzol reagent (Cat No. 15596-018, Ambion Life Technologies) according to the manufacturer's protocol. The total RNA pellet was airdried for 8 minutes and dissolved in an appropriate volume of nuclease free water (Cat No. AM9937, Ambion life technologies) followed by a total RNA quantification using the Nanodrop UV-VIS Spectrophotometer (Thermo Scientific). The total RNA was further purified using the MinElute Cleanup Kit (Cat No. 74204, Qiagen) according to the manufacturer's instructions. Quality and quantity of the total RNA was assessed by the 2100 Bioanalyzer using a Nano chip (Agilent, Santa Clara, CA). Total RNA samples having RNA Integrity Number (RIN)>8 were subjected to library generation.

TruSeq Stranded mRNA Sample Preparation

Strand-specific libraries were generated using the TruSeq Stranded mRNA sample preparation kit (Illumina Inc., San Diego, RS-122-2101/2) according to the manufacturer's instructions (Illumina, Part #15031047 Rev. E). Briefly, polyadenylated RNA from intact total RNA was purified using oligo-dT beads. Following purification the RNA was fragmented, random primed and reverse transcribed using SuperScript II Reverse Transcriptase (Invitrogen, part #18064-014) with the addition of Actinomycin D. Second strand synthesis was performed using Polymerase I and RNaseH with replacement of dTTP for dUTP. The generated cDNA fragments were 3' end adenylated and ligated to Illumina Paired-end sequencing adapters and subsequently amplified by 12 cycles of PCR. The libraries were analyzed on a 2100 Bioanalyzer using a 7500 chip (Agilent, Santa Clara, CA), diluted and pooled equimolar into a 15-plex, 10 nM sequencing pool and stored at −20° C.

RNA-Seq Data Processing

RNA-Seq raw reads Fastq were aligned to the Ensembl reference genome (Homo_sapiens.GRCh38.dna.primary_assembly) with TopHat (version 2.0.12, Bowtie version 1.0.0, Samtools version: 0.1.19). Read counts were generated by HTseq-count with uniquely mapped reads. Unmapped reads were discarded. Sequence reads were normalized to 10 million reads per sample and log 2 transformed with the formula, log 2(((expression gene x÷library size) 106)+1), where the library size was the sum of all expression values per sample. Read-counts were further analyzed by Qlucore Omics Explorer (3.1) for differential expression.

Cell Cultures and Functional Assays.

Cells were cultured for various times with anti CD3/CD28 beads (Miltenyi: 3 beads:1 cell ratio), 300 IU/ml IL-2 and with or without 100 nm rapamycin in IMDM (Lonza), supplemented with 10% FCS, 1% Penicillin/streptomycin and 1% L-glutamine. For functional assays (cytokine production, suppression) cells were taken off rapamycin (where needed) and rested overnight in medium with IL-2. For intracellular cytokine staining, cells were stimulated with PMA (20 ng/ml) and Ionomycin (1 uM) in the presence of Golgi-Plug for 4 hours at 37° C. and subsequently stained using the intracellular cytokine.

Results

Different CD4 T Cell Populations are Distinguished by Expression of CD45RA and CD25

Five CD4 T cell populations can be identified among peripheral blood mononuclear cells (PBMC) from healthy human donors, based on expression of the CD25 and CD45RA surface markers (FIG. 1) [Miyara, M., et al. 2009]. Two of these populations contain Tregs. $CD25^+CD45RA^+$ CD4 T cells are known as naïve Tregs (nTregs-marked in red and indicated with 1 in FIG. 1). These cells have never been activated and are, by definition, probably thymic derived. A second population of Tregs is identified on the basis of a $CD25^{high}CD45RA^-$ expression profile (eTregs, marked in orange and indicated with 2 in FIG. 1). These cells have been activated before and consist of a mixture of activated tTregs and iTregs. Other CD4 T cell populations in our analysis include the CD45RA+CD25-naïve Tconv cells (dark blue and indicated with 4 in FIG. 1) and $CD45RA^- CD25^-$ effector/memory Tconv cells (light blue and indicated with 5 in FIG. 1). Finally, a population of $CD25^+CD45RA^-$ cells (P3-green and indicated with 3 in FIG. 1) was analyzed. Separation of these latter cells from effector Tregs (eTregs) is somewhat arbitrary on basis of the used markers. Although expression of CD127 can be taken along as an additional marker, this still does not allow unequivocal separation of the two populations, as some of the P3 cells are $CD127^-$ [Pesenacker, A. M., et al. 2013]. Despite their phenotypic similarity, eTregs and P3 cells have dramatically different functional capacities. Whereas eTregs suppress immunity and lack the capacity to make inflammatory cytokines, P3 cells do make inflammatory cytokines and are not suppressive [Miyara, M., et al. 2009; Pesenacker, A. M., et al. 2013; Ayyoub, M., et al. 2009]. In fact, whereas the presence of bona fide Tregs in tumors is associated with poor prognosis, the reverse is true for the presence of these P3 cells, underlining the functional difference between these phenotypically similar populations of T cells [Saito, T., et al. 2016].

The FoxP3 transcription factor governs differentiation and maintenance of the Treg lineage. All Tregs express this factor and its stable expression is critical for Treg function. Loss or even reduction of FoxP3 expression results in conversion to Tconv [Wan, Y. Y. and R. A. Flavell 2007; Feng, Y., et al. 2014]. As shown in FIG. 1 (bottom), both nTregs and eTregs express this factor, whereas nTconv and mTconv do not. Most cells in the P3 population express low levels of FoxP3, but this expression is not associated with regulatory capacity in these cells [Miyara, M., et al. 2009]. A small proportion of cells in the P3 gate expresses high levels of FoxP3 and may represent "contaminating" eTregs (FIG. 1, bottom). A second transcription factor associated with Tregs is Helios. In mice, expression of Helios marks (stable) tTregs [Thornton, A. M., et al. 2010]. However, in human Tregs, expression of Helios can be induced in HeliosTregs upon activation, making it an unsuitable marker to identify tTregs [Himmel, M. E., et al. 2013]. It should be noted, furthermore, that expression of these transcription factors cannot be used to isolate viable Tregs. As these molecules reside intracellularly, their detection requires permeabilization of the cell membrane and fixation of the cells, procedures that are inconsistent with viability.

GPA33 Marks a Subset of Tregs

Figure 2A:
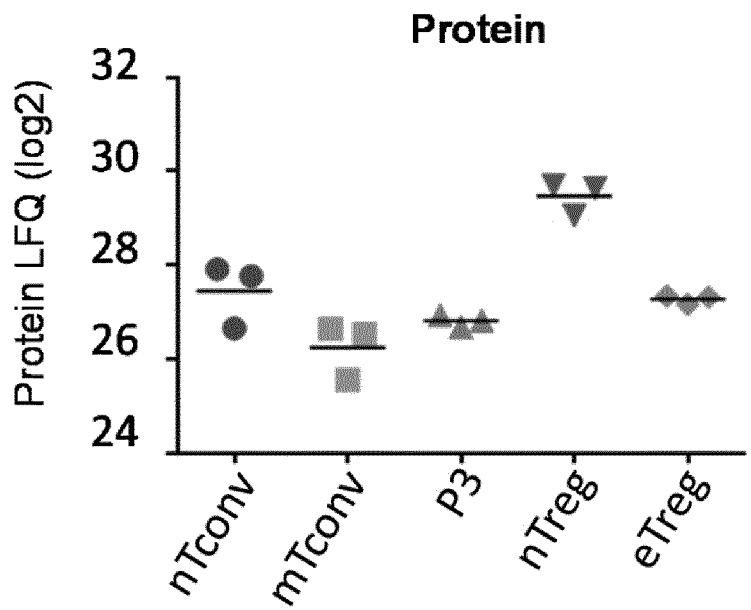
FIG. 2; Quantification of proteins by Mass Spectrometry. (A) FACS-purified CD4$^+$ subsets were lysed and protein abundance was determined by Mass Spectrometry. Absolute protein abundance was estimated using the label free quantitation (LFQ) methodology. Intensity values were log 10 transformed. (B) GPA33 mRNA levels were determined by RNAsequencing and expressed as relative values.
Figure 2B:
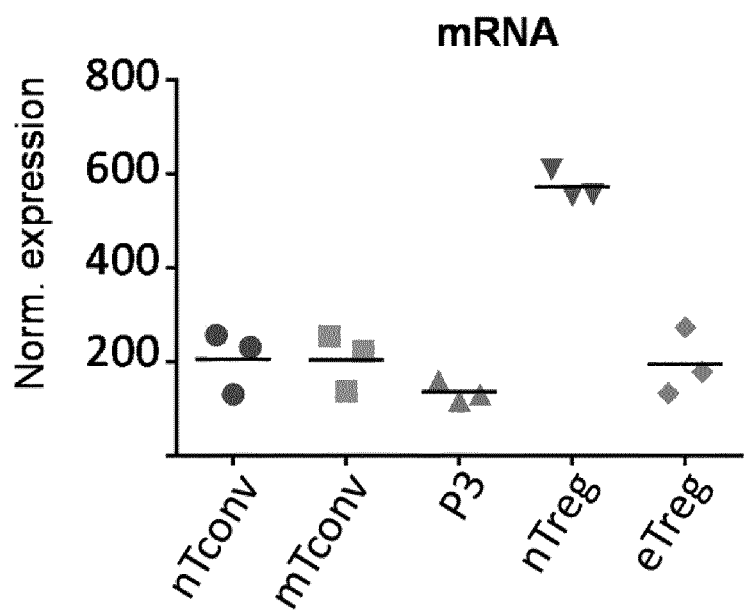

To identify novel surface markers that allow purification of specific Treg populations, we performed whole cell quantitative Mass Spectrometry (MS) on the five CD4 T cell types defined by CD25 and CD45RA expression. Subsets were isolated by FACSorting and subsequently analysed by MS. In this analysis, we found that the surface molecule GPA33 is preferentially expressed in the nTreg population, at levels that fall within the range of well-known T cell surface molecules such as CD4, CD27 and CD28 (FIG. 2A). Although the other CD4 T cell populations also express this molecule, levels are about 10-fold lower than those found in nTregs. Preferential expression of GPA33 in the nTreg subset was also reflected at the mRNA level (FIG. 2B). Because MS measures protein concentrations from lysates, this lower expression level could represent the presence of fewer molecules per cell or the presence of this marker on a smaller proportion of the cells (or a combination thereof).

Figure 3:
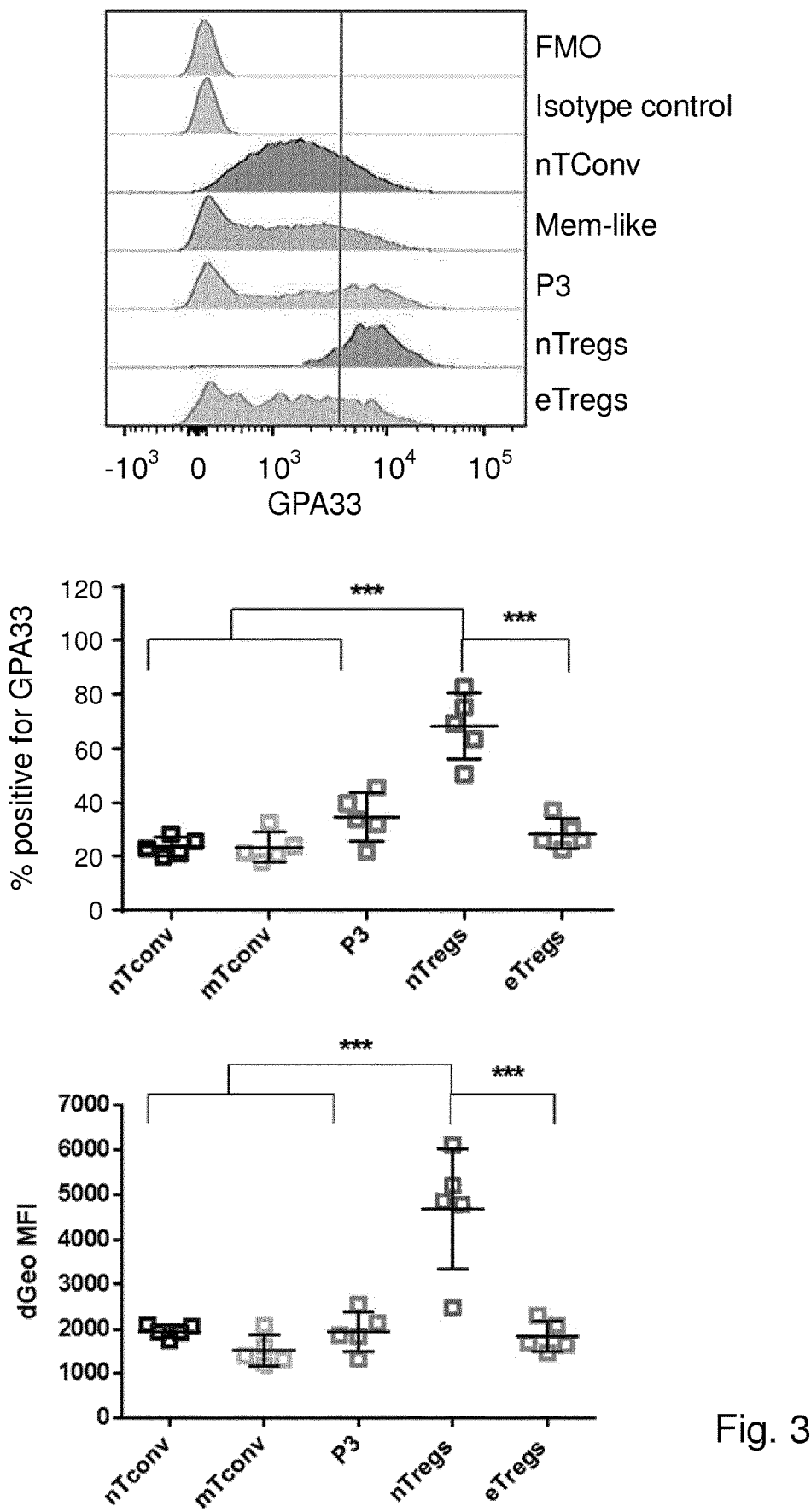
FIG. 3: Expression profiles for GPA33 on the five CD4 T cell populations in human blood. PBMCs were isolated and stained as in FIG. 1. Shown are GPA33 profiles of the populations defined by CD45RA/CD25 expression profiles as shown in FIG. 1 (top plot), percentages of GPA33 expressing cells compared to isotype control (middle plot), and mean fluorescence intensities of GPA33 staining on the different populations (bottom plot). Note matching color codes throughout figure. Data in bottom two panels represent five different donors, each indicated by individual symbols. Statistical comparisons were performed by one-way ANOVA, followed by Tukey's HSD. ***=p≤0.0001.

GPA33 is a transmembrane glycoprotein related to CD2 and its expression on T cells has not been reported previously. Flow cytometry using a fluorescently labelled antibody showed that expression of GPA33 is not by itself specific for Tregs, as nTconv and a proportion of mTconv also express this marker (FIG. 3). Nonetheless, levels of GPA33 are much higher on nTregs, with a minor population exhibiting low expression (FIG. 3). Subsets of eTregs and P3 cells also expressed high levels of GPA33, but the majority of these cells expressed intermediate levels or even lacked expression of this marker altogether (FIG. 3).

Figure 4:
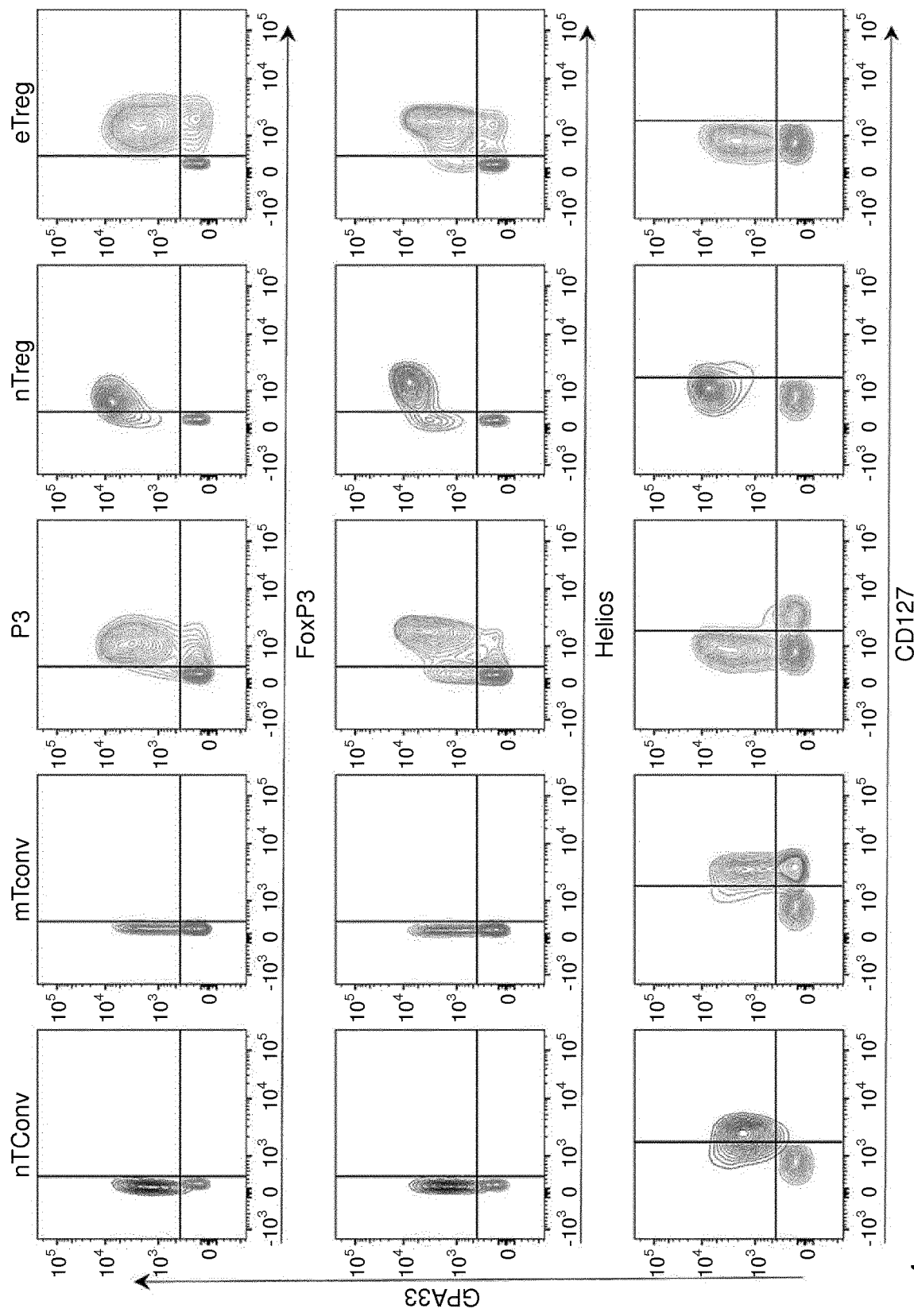
FIG. 4: GPA33$^{high}$ cells express FoxP3 and Helios, and lack CD127. PBMCs were gated on single, live, CD4$^+$ T-cells and then delineated into naive Tconv, memory-like Tconv, P3, naive Tregs and effector Tregs based on surface expression of CD45RA and CD25. Expression of GPA33 against FoxP3 (top), Helios (middle) and CD127 (bottom) per population is shown. Grey contours represent isotype control staining. Data are representative of 5 blood donors.

Tregs express low levels of CD127, the alpha chain of the IL-7 receptor. Indeed, both nTconv and mTconv populations are almost universally CD127$^+$, whereas nearly all nTreg and eTreg populations lack expression of this marker. Remarkably, within the P3 population, high expression of GPA33 was exclusively found on CD127-cells (FIG. 4). Furthermore, high levels of GPA33 were found only on cells also expressing FoxP3 and Helios, although vice versa not all FoxP3 and Helios expressing cells were GPA33$^+$ (FIG. 4). Together, this expression pattern shows that high expression of GPA33 marks a population of FoxP3$^+$Helios$^+$CD127$^-$ Tregs, but that not all Tregs express this marker.

GPA33$^{high}$ Tregs Lack Ability to Produce Effector Cytokines

Figure 5A:
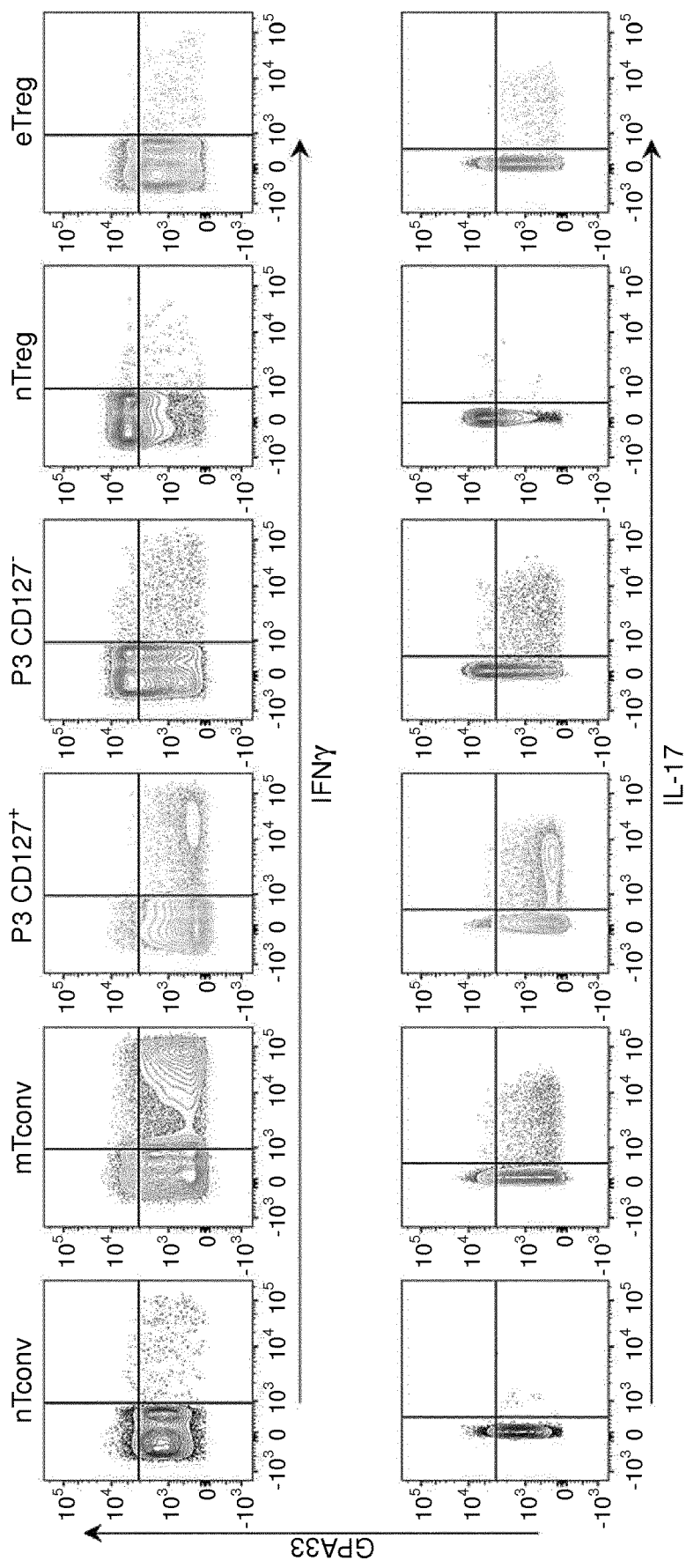
FIG. 5: GPA33$^{high}$ cells do not produce effector cytokines. FACSorted nTconv, mTconv, P3 (CD127$^+$ and CD127$^-$), nTregs and eTregs were stimulated with PMA and Ionomycin for 4 h and then stained intracellularly for IFNγ (top) and IL-17 (bottom). Data in A are representative profiles and B cumulative results of 4 blood donors, showing mean+/−SD for GPA33$^{high}$ cells (in green/light grey) and GPA33$^{int/low}$ cells (in red/dark grey). Statistical comparisons were performed by Welch's T-test (two-tailed, GPA33 high vs GPA33 low). *=0.05≤p<0.01; **=p≤0.01.
Figure 5B:
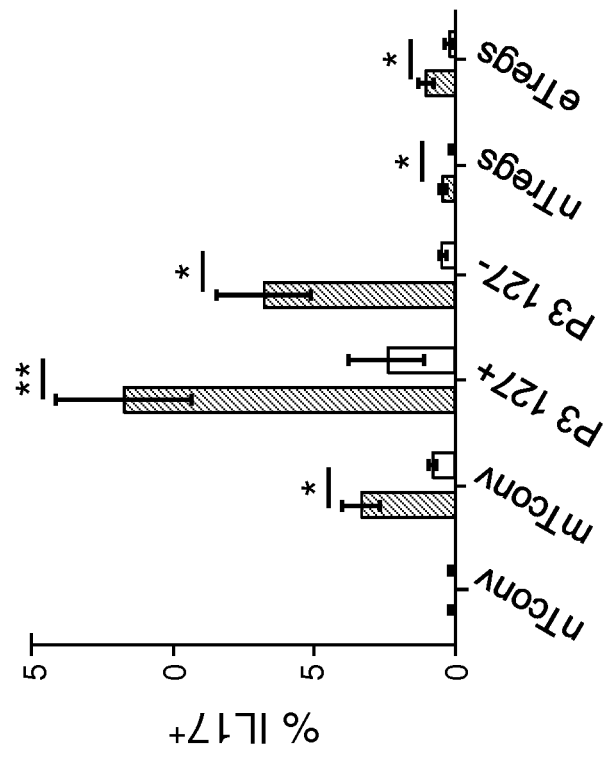
Figure 5B:
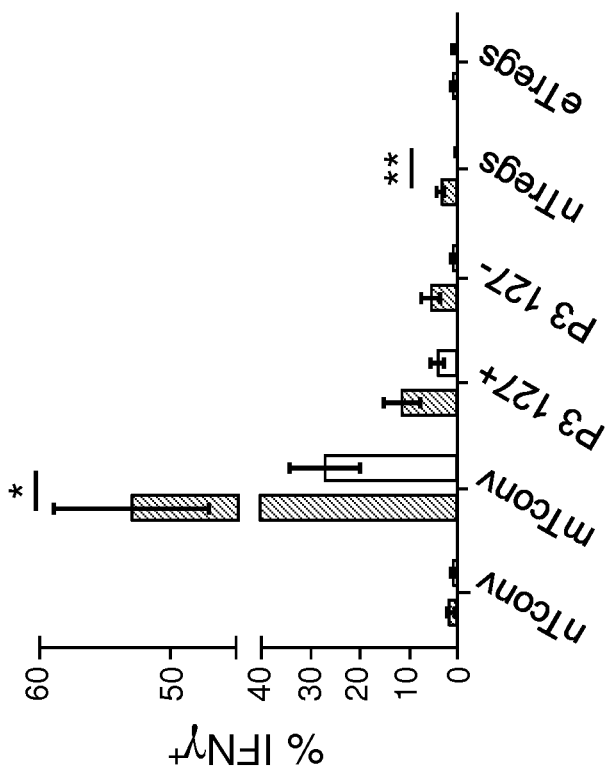

As a population, Tregs produce little effector cytokines, such as IFNγ and IL-17. Interestingly, those few cells in the nTreg and eTreg populations that did produce these cytokines were mostly confined to the GPA33 negative and intermediate populations. This effect was most prominently visible in the CD127$^-$ P3 population. Ability to produce these cytokines in this population was inversely correlated with expression of GPA33, with those cells expressing the highest levels of this marker exhibiting hardly any detectable cytokine production at all (FIG. 5). High expression of GPA33 on CD127$^-$ CD4 T cells (nTreg, eTreg and P3) thus marks a population that possesses the lowest capacity to produce effector cytokines.

Figure 6A:
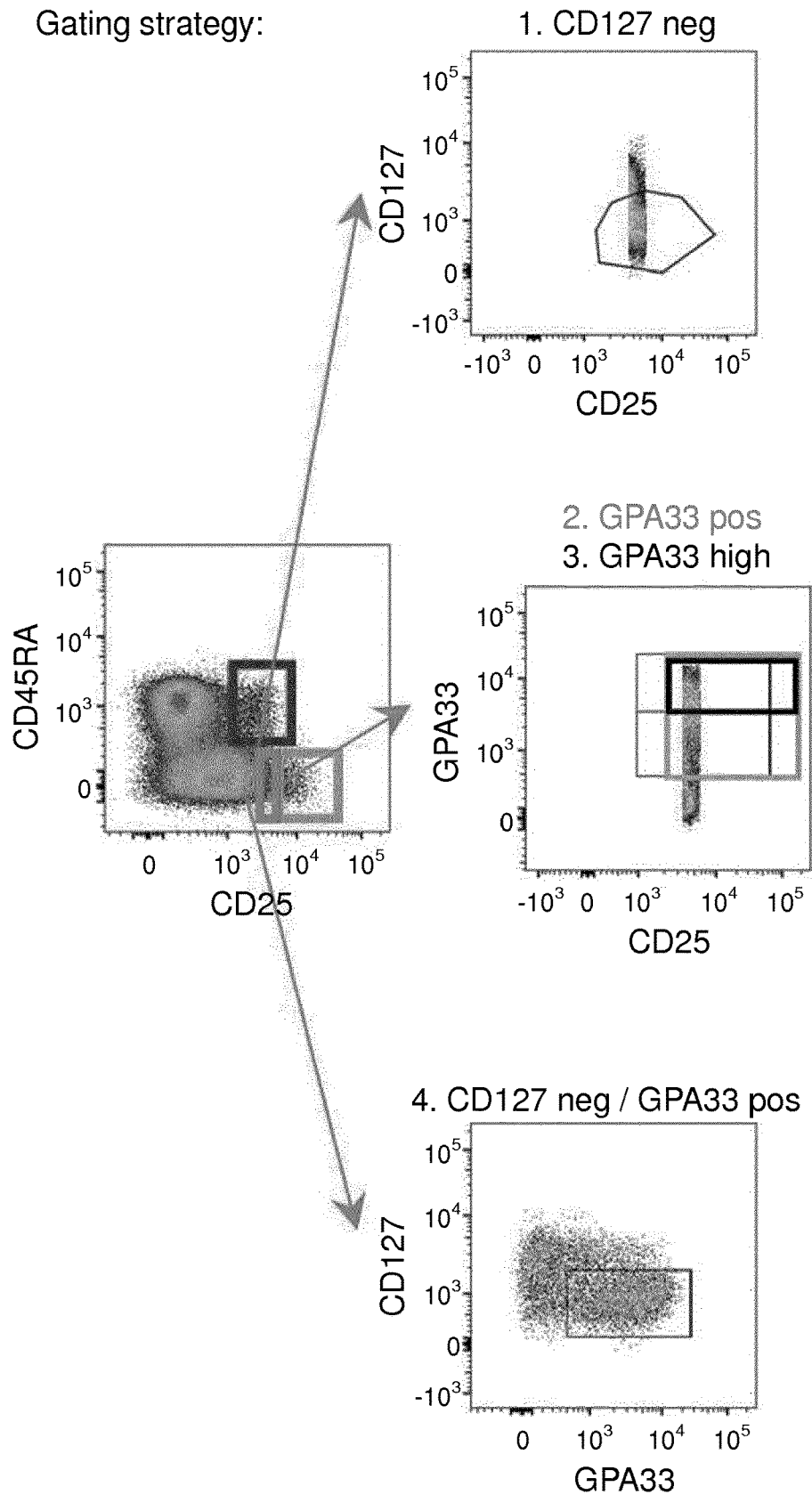
FIG. 6: Selection for GPA33$^{high}$ cells improves purity of FoxP3$^+$Helios$^+$ population. CD4$^+$ T-cells were delineated into P3, naive Tregs and effector Tregs based on CD25 and CD45RA expression. (A) Each population was then further subdivided into either CD127 (1.), GPA33int (2.), GPA33$^{high}$ (3.; defined as the gate that captures 75% of naive Tregs) or CD127$^-$GPA33+ (4.). The % purity (frequency of parent gate) are shown for FoxP3+ cells (B) and Helios+ cells (C). Data are representative of 4 donors and show mean+/−SD. Statistical comparisons were performed by one-way ANOVA, followed by Tukey's HSD. *=p≤0.0001; =0.01<p≤0.001; *=0.05<p≤0.01.
Figure 6B:
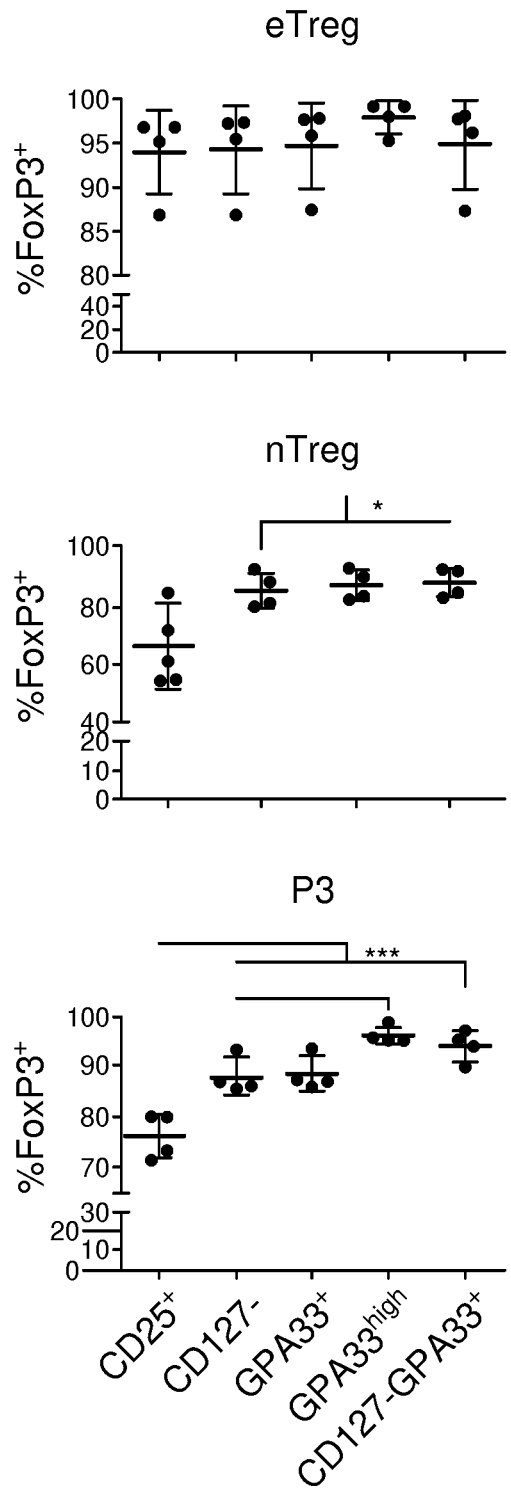
Figure 6C:
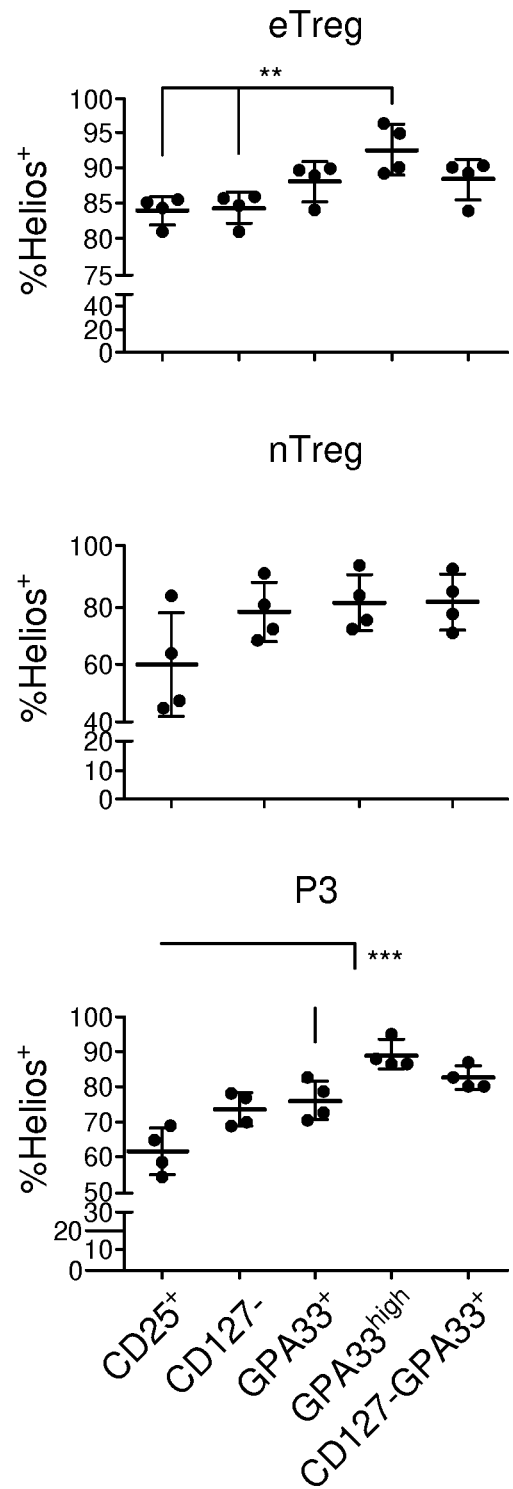

Selection for GPA33$^{high}$ Tregs results in a purer and more stable population One of the challenges for adoptive cellular therapy with Tregs is that Treg preparations are gradually overgrown by Tconv, unless rapamycin is added, which suppresses expansion and may alter functional properties [Hippen, K. L., et al. 2011]. This overgrowth might be explained both by conversion of Tregs into Tconv as well as by contamination of the starting Treg population with Tconv. We reasoned that selection for high expression of GPA33 might result in isolation of a purer Treg population. Indeed, selection for high expression of this marker (defined as the level at which 75% of nTregs are GPA33+) markedly elevated the proportion of FoxP3$^+$ and Helios$^+$ cells compared to selection for CD25$^+$ alone. Purity was improved even compared to selection based on the CD25$^+$CD127$^-$ profile, which is used for current clinical preparations [Trzonkowski, P., et al. 2015; Bluestone, J. A., et al. 2015]. This greater purity was most prominent within the eTreg and P3 populations (FIG. 6).

Figure 7A:
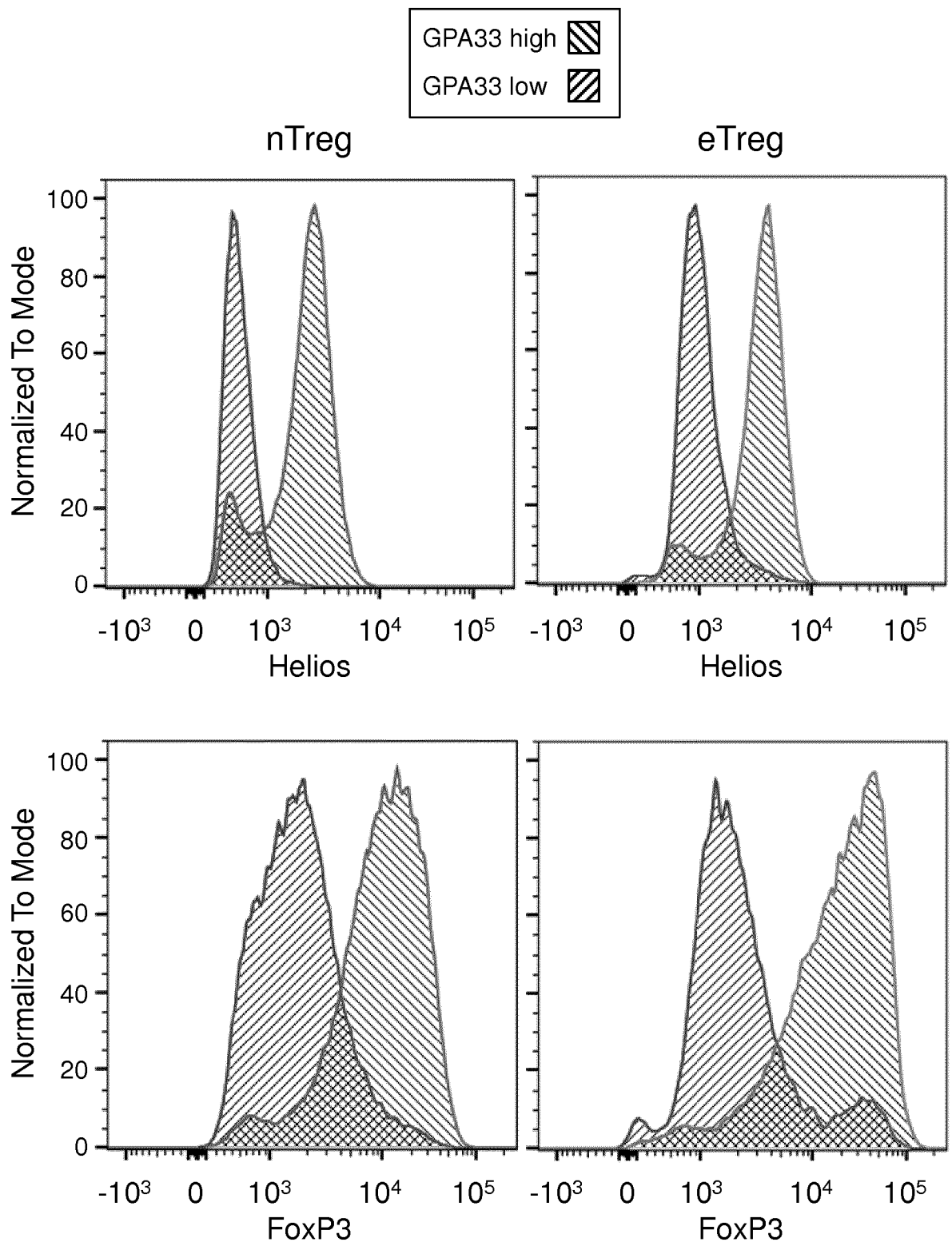
FIG. 7: GPA33 marks a population of stable Tregs. Naïve (nTregs) and effector Tregs (eTregs) (identified as in FIG. 1) were sorted into GPA33$^{high}$ (defined as in FIG. 6—green/light grey histograms) and GPA33$^{low}$ (red/dark grey histograms) populations and subsequently activated in vitro with anti-CD3+anti-CD28 coated beads in the presence of 100 U/ml IL-2. (A) After 7 days culture, nTreg derived T cells were analyzed for expression of FoxP3 (bottom) and Helios (top) by intracellular staining as in FIG. 1. (B) GPA33low, GPA33high or total n'Treg cells were cultured as in A in the presence or absence of Rapamycine. After one week, cells were restimulated for 6 hours with PMA and Ionomycin and production of IFNγ (top) and IL-17 (bottom) was measured by intracellular flow cytometry. Percentages of cytokine producing cells are shown.
Figure 7B:
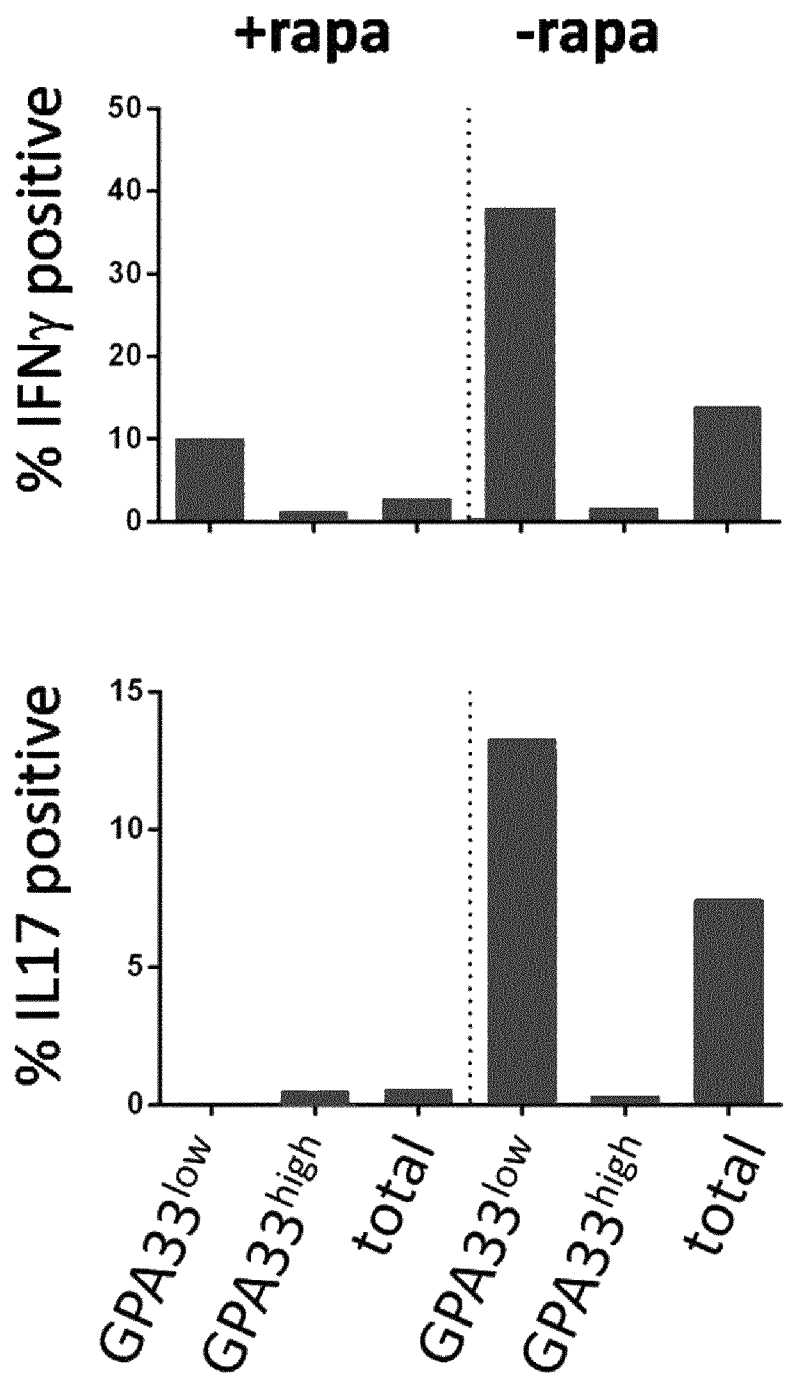

To test whether selection for high expression of GPA33 allows for expansion of a more stable Treg population, we isolated GPA33$^{high}$ and GPA33$^{low}$ CD25$^+$ cells from the nTreg and the eTreg subsets and examined expression of FoxP3 and Helios after one week of culture. Clearly, GPA33$^{low}$ cells almost uniformly lost expression of both these markers, whereas GPA33$^{high}$ cells mostly retained expression of these markers (FIG. 7A). This result was all the more remarkable, because no rapamycin had been added to these cultures to favour expansion of Tregs over Tconv. Selection for GPA33$^{high}$ cells also allowed for expansion of nTregs that stably lacked ability to produce effector cytokines. While the presence of rapamycin suppressed most cytokine production also in GPA33$^{low}$ nTregs or in unfractionated nTregs, in its absence, both these populations produced clearly detectable levels of IL-17 and IFNγ. No such production was observed in cultures seeded with GPA33$^{high}$ cells, however (FIG. 7B). Finally, expanded GPA33$^{high}$ nTreg cells readily suppressed proliferation of Tconv in a standard in vitro suppression assay, whereas the expanded GPA33$^{low}$ nTreg cells lacked this ability and in fact stimulated proliferation of such cells (data not shown). Together, these results show that the GPA33$^{high}$ nTreg population consists of cells that are stably committed to the Treg lineage, whereas the GPA33$^{int}$ and GPA33$^{low}$ populations are much less stable and/or contaminated with Tconv.

Figure 8A:
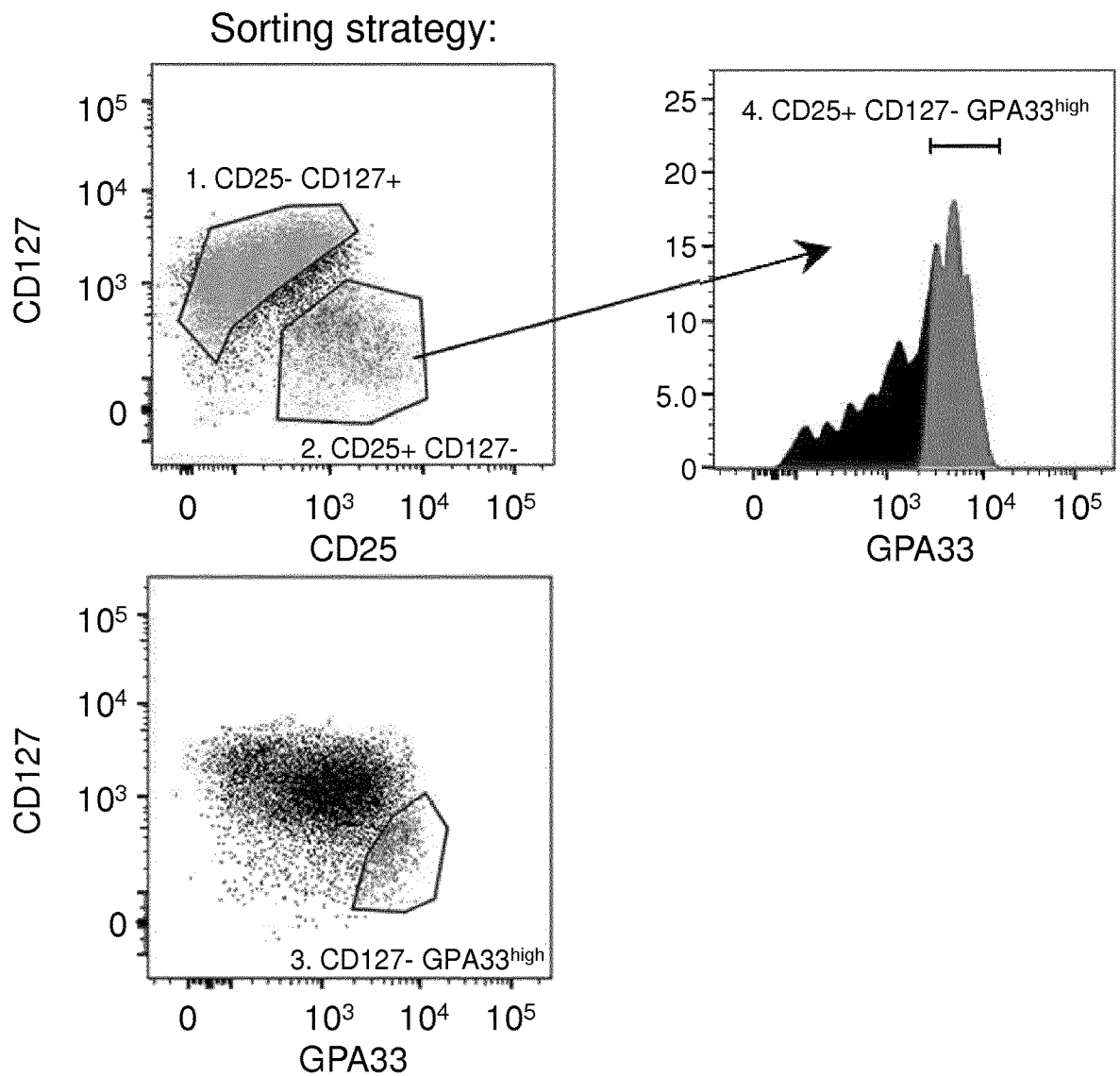
FIG. 8: Selection for GPA33$^{high}$ Tregs yields more stable expanded Tregs than current criteria. CD4 T cells were sorted according to different gating strategies combining CD25, CD127 and GPA33 into: CD25$^-$CD127$^+$ Tconv (1), CD25$^+$CD127$^-$ Tregs (2), CD127$^-$GPA33$^{high}$ Tregs (3) and CD25$^+$CD127$^-$GPA33$^{high}$ Tregs (4) (A). Cells were then cultured with anti CD3/CD28 beads (3 beads: 1 cell), 300 IU/ml IL-2 and with or without 100 nm rapamycin. On day 7, cells were stained for FoxP3 and Helios (B). Numbers indicate % of cells positive for FoxP3 and Helios, respectively. The rest of the cells were taken off rapamycin (where needed) and rested overnight in medium with IL-2. The next day, these cells were stimulated with PMA (20 ng/ml) and Ionomycin (1 uM) in the presence of Golgi-Plug for 4 h at 37° C. to assess production of IFNγ, IL-2 and IL-17 (C).
Figure 8B:
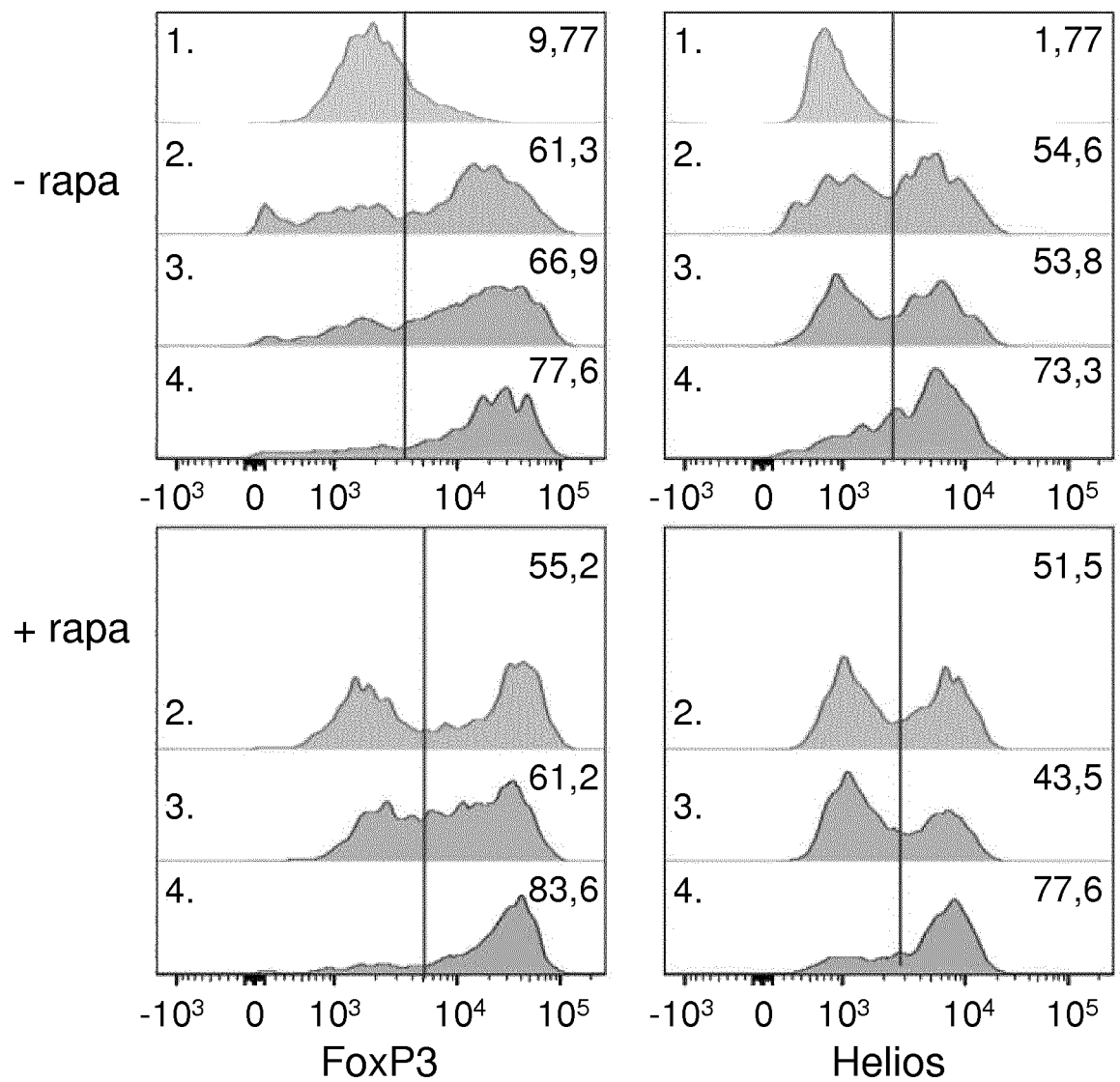
Figure 8C:
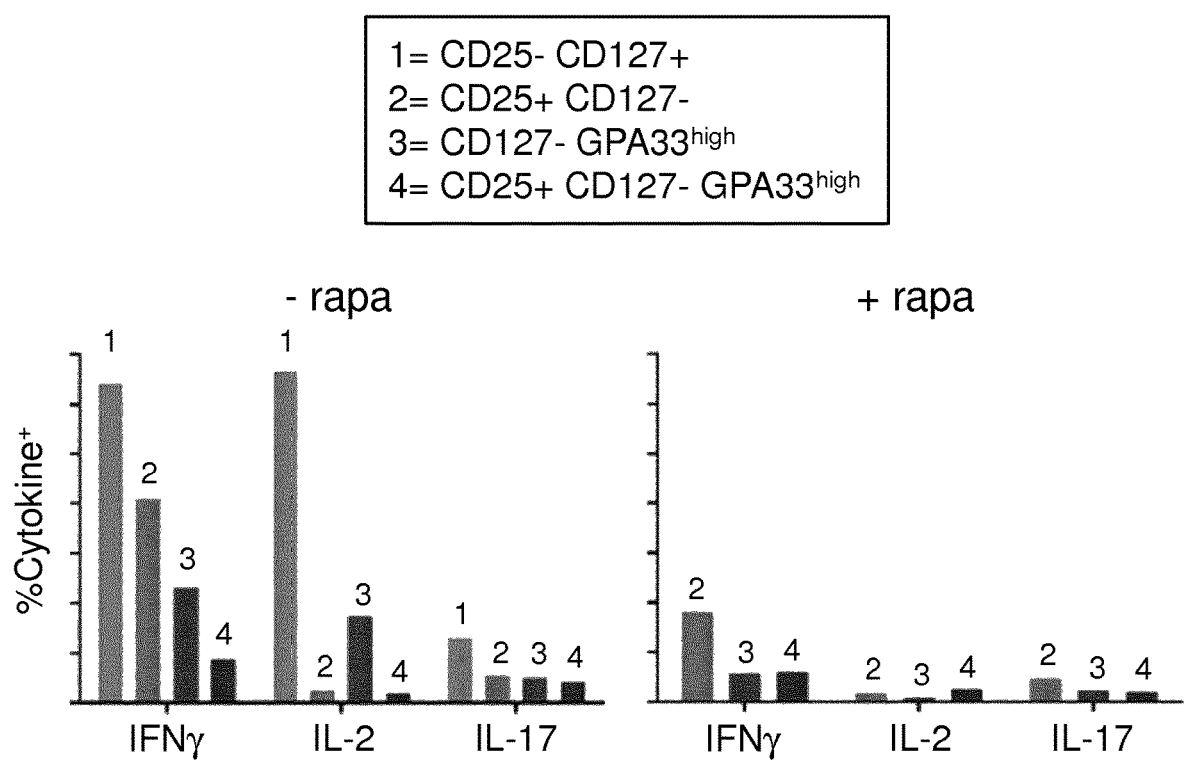

These findings suggested that selection for GPA33$^{high}$ cells might improve the stable Treg content of cultures compared to selection criteria currently used to isolate clinical grade Tregs [Trzonkowski, P., et al. 2015; Bluestone, J. A., et al. 2015]. To put this to the test, we activated CD25$^-$CD127$^+$ Tconv, CD25$^+$CD127$^-$ Tregs, CD127$^-$ GPA33$^{high}$ and CD25$^+$CD127$^-$GPA33$^{high}$ cells in the presence or absence of rapamycin and measured expression of FoxP3 and Helios after one week of culture. Selection for GPA33$^{high}$CD127$^-$ T cells improved the percentage of FoxP3$^+$ and Helios$^+$ cells compared to the traditionally used CD25$^+$CD127$^-$ criteria (FIG. 8A,B). However, the greatest percentage FoxP3$^+$ and Helios$^+$ cells was obtained when all three criteria were combined. Indeed, both in the presence and absence of rapamycin, cultures of CD25$^+$CD127$^-$GPA33$^{high}$ cells contained the greatest proportion of FoxP3$^+$ and Helios$^+$ cells. This was also reflected in the ability to produce effector cytokines. Whereas Treg cultures starting with the traditional criteria yielded many cells producing such cytokines, especially in the absence of rapamycin, hardly any cytokine producing cells emerged from cultures started with CD25$^+$CD127$^-$GPA33$^{high}$ cells (FIG. 8C).

Expanded CD25$^+$CD127$^-$GPA33$^{high}$ Tregs are Suppressive

Figure 9A:
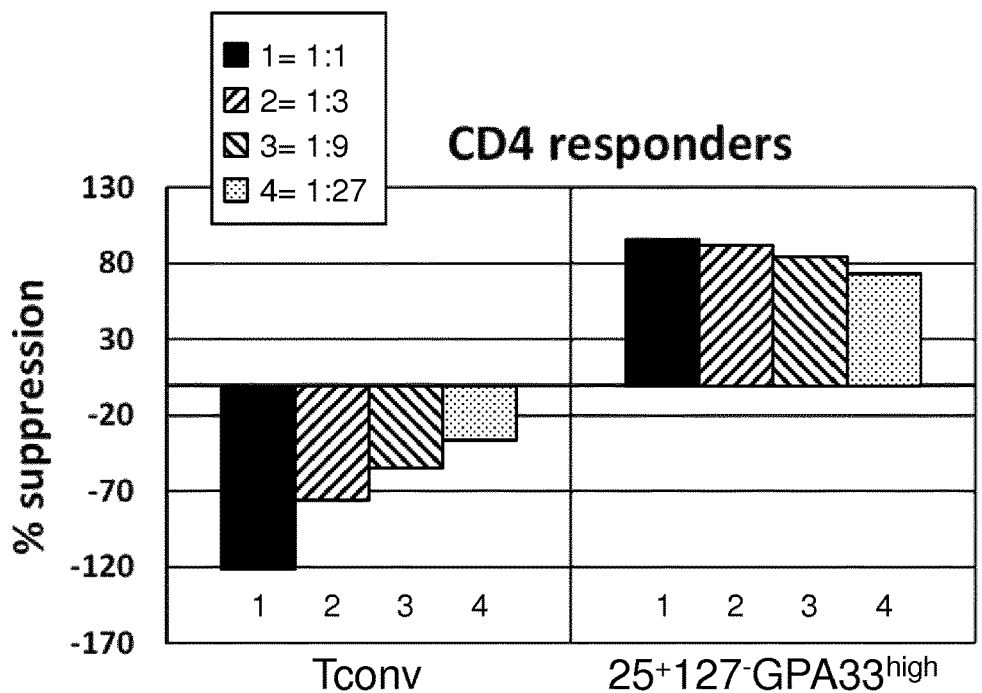
FIG. 9: GPA33 selected Tregs are fully suppressive after expansion. CD25$^+$CD127$^-$GPA33$^{high}$ Tregs and CD25$^-$CD127$^+$ Tconv were expanded in vitro with antibodies to CD3 and CD28 and IL-2 for two weeks without rapamycin. Subsequently, expanded Tregs were cultured in different ratios with CFSE labelled PBMC in the presence of anti CD3 and anti CD28. After 4 days, CFSE profiles of CD4$^+$ (A) and CD8$^+$ responder T cells (B) were measured by flow cytometry.
Figure 9B:
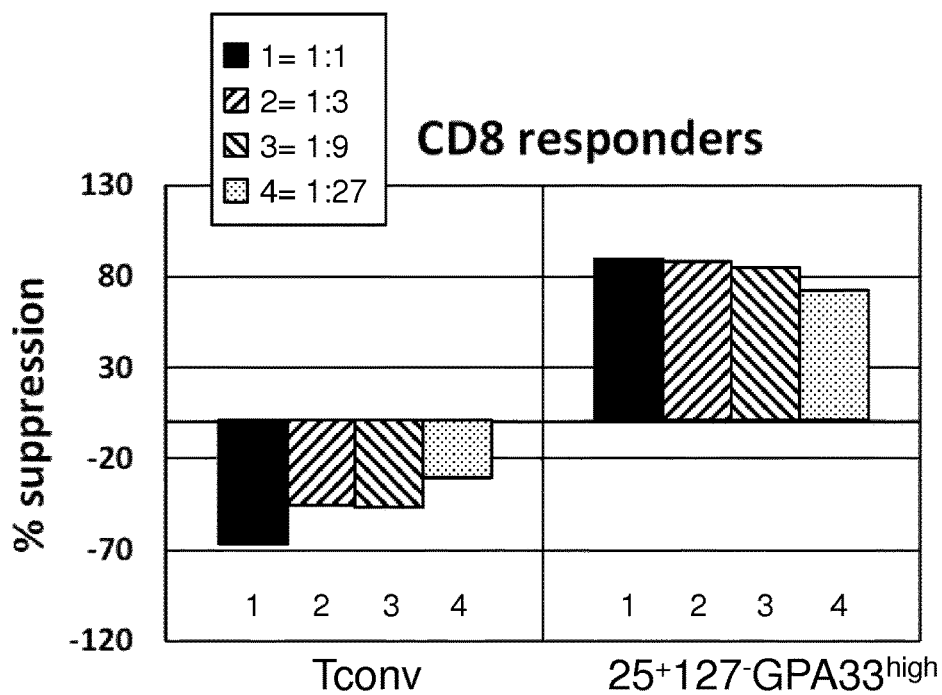

For use in adoptive cellular therapies, an essential question is whether expanded Tregs retain the ability to perform their suppressive functions. The gold standard in vitro test for this is to activate Tconv in the presence of different numbers of Tregs. Using this test, we show that CD25$^+$CD127 GPA33$^{high}$ cells, cultured for two weeks without rapamycin, strongly suppress proliferation of both CD4$^+$ and CD8$^+$ Tconv even at low ratios of Treg to Tconv, (FIG. 9).

Induced Tregs do not Express High GPA33

Figure 10:
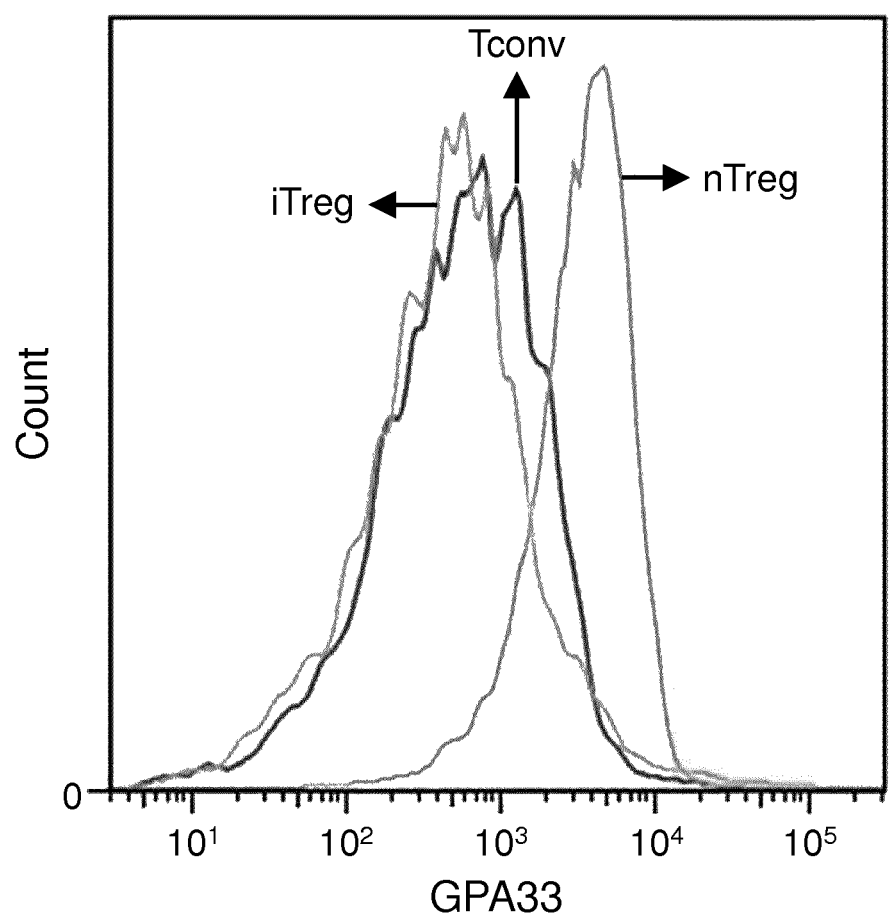
FIG. 10: GPA33 is not expressed on iTregs. Tconv CD4 T cells were stimulated with antibodies to CD3 and CD28 in the presence of TGFβ to produce iTregs (red histogram), or without (yellow histogram). As reference, nTregs (blue histogram) were also grown under the same conditions (without TGFβ). After 14 days, cells were restimulated with anti CD3 and anti CD28 in the presence of IL-2. Expression of GPA33 was measured on day 18 by flow cytometry. For iTregs, cells were gated on FoxP3$^+$ cells.

It is believed that tTregs are more stably committed to the Treg lineage than iTregs [Sakaguchi, S., et al 2008]. Given the profound stability of GPA33$^{high}$ cells in tissue culture, it is conceivable that this surface molecule marks the human tTreg population. Although it is not currently possible to unequivocally identify iTregs in primary human samples, such cells can be generated in vitro by culturing CD4 Tconv in the presence of TGFβ [Kanamori, M., et al. 2016]. These conditions induce differentiation of FoxP3, but not Helios expressing cells that possess suppressive capacity towards Tconv [Kanamori, M., et al. 2016]. Despite developing into Tregs, such cells do however not acquire high expression of GPA33 (FIG. 10). On the other hand, upon 7 day culture in vitro, nTregs maintain high expression of GPA33 (FIG. 10). Together, these findings are consistent with the notion that GPA33 stably marks the human tTreg population.

Expression of GPA33 Distinguishes Between Cells that do and do not Produce IL-17 in Population 3.

Figure 11:
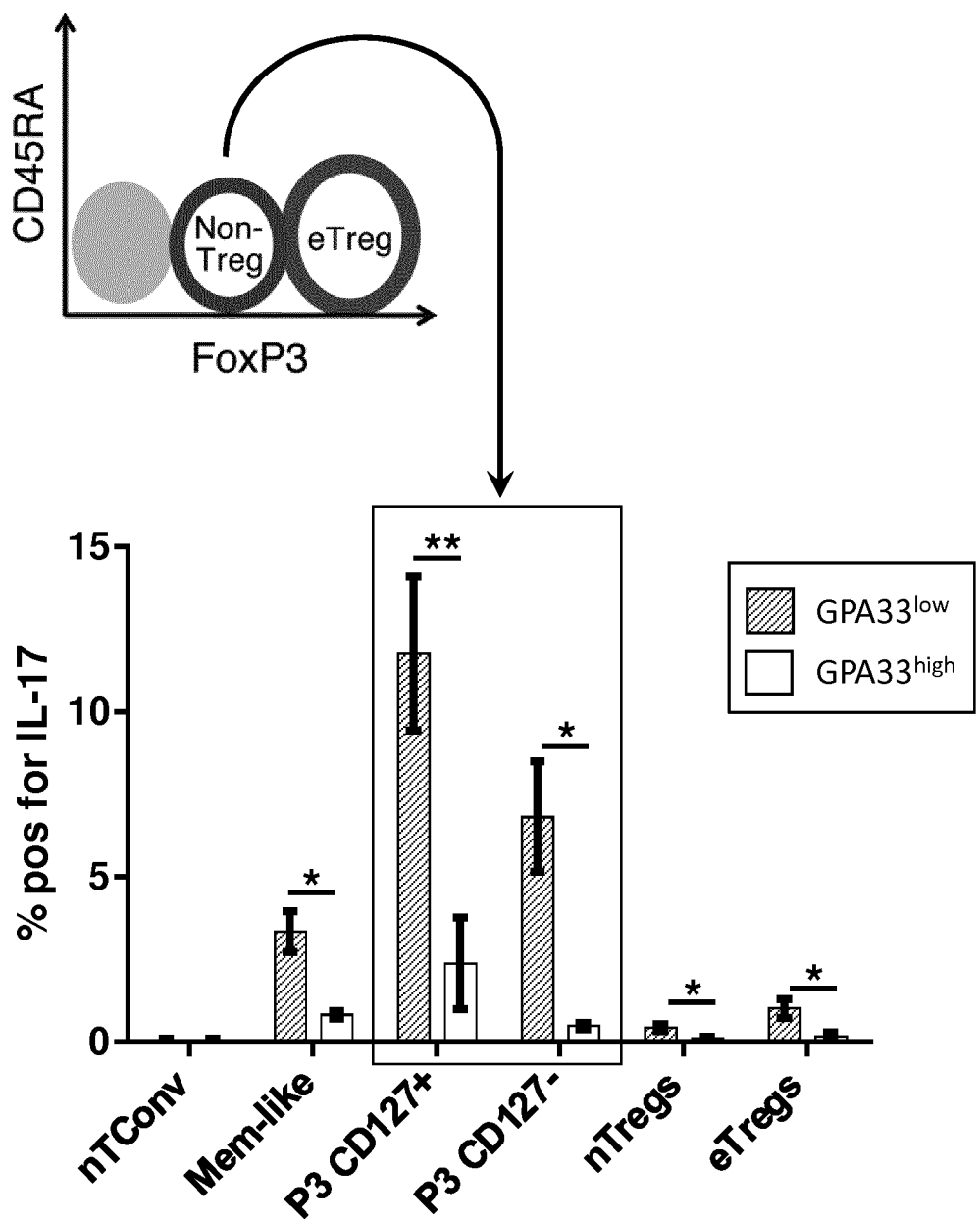
FIG. 11: GPA33 distinguishes between IL-17 producing and non-producing FOXP3$^+$ T cells in Population 3. CD4$^+$ T cells from human blood were stimulated with PMA (20 ng/ml) and Ionomycin (1 μM) in the presence of Golgi-Plug for 4 h at 37° C. to assess production of IL-17. Gating on the CD45RA$^-$FOXP3$^{int}$CD25$^{int}$CD4$^+$ population (that defines Population 3) shows that there is an inverse correlation between GPA33 expression and IL-17 cytokine production.

A subset of human CD4$^+$ T cells (referred to as P3) expresses hallmarks of Tregs (FOXP3 and CD25), but nonetheless exhibits Tconv functions [Miyara, M., et al. 2009]. These cells for instance readily produce high levels of IL-17 even when they are CD127$^-$ and therefore correspond to the commonly used Treg profile (FIG. 11). On the other hand, eTregs do not produce IL-17 (FIG. 11). Importantly, all IL-17 producing cells were found in the GPA33$^-$ subpopulation, regardless of the expression of CD127, whereas GPA33$^+$ cells always lacked the ability to produce this cytokine.

The presence of genuine Tregs in tumors is a poor prognostic marker. In contrast, the presence of P3 cells in colon carcinoma is associated with favourable disease progression [Saito, T., et al. 2016]. It is believed that the Tconv activity of these cells helps immune attack on the tumor. Our results show that measurement of GPA33 helps distinguish between the cells with Tconv properties (GPA33$^-$) in P3 and those without (GPA33$^+$). Inclusion of this marker is therefore expected to allow more reliable prognostic diagnosis of colon carcinoma with those patients exhibiting high frequencies of infiltrating P3 cells lacking GPA33 expression having the most favourable prognosis.

GPA33 is Differentially Expressed on Dysfunctional Tregs in Autoimmune Disease

Figure 12:
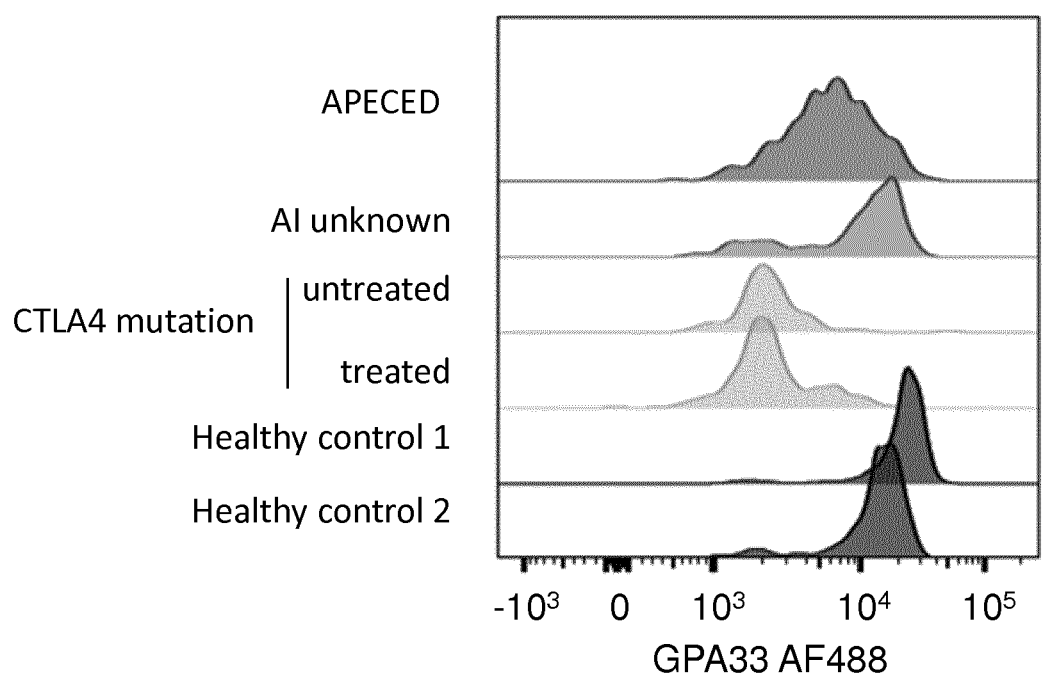
FIG. 12: GPA33 expression in nTregs isolated from blood of patients suffering from autoimmune diseases and healthy controls. APECED is autoimmune polyendocrinopathy-candidiasis-ectodermal dystrophy; AI is autoimmune disease. The patient with the CTLA4 mutation was tested before treatment or after treatment with recombinant CTLA4-Ig, which mitigated disease.

The Aire transcription factor regulates expression of self antigens in thymic medullary epithelial cells, necessary to drive differentiation of self reactive thymocytes into the Treg lineage. Aire deficiency causes massive autoimmune disease in mice due to the inability to generate such Tregs [Sakaguchi, S., et al 2008]. Likewise, mutations in the gene encoding Aire cause development of an autoimmune syndrome known as autoimmune polyendocrinopathy-candidiasis-ectodermal dystrophy (APECED). Some Tregs do still develop when Aire is deficient, but are clearly unable to prevent development of pathology. Interestingly, the nTregs that still develop in APECED patients have reduced expression of GPA33 (see FIG. 12).

Reduced expression of GPA33 is similarly found on Tregs from patients with a congenital autoimmune disorder caused by a loss of function mutation in the gene encoding CTLA4, a protein that is necessary for proper Treg function [Sakaguchi, S., et al 2008]. Expression of GPA33 is however not always reduced in patients with autoimmune disease, as nTregs from another patient with autoimmune disease of unknown etiology had normal cell surface levels of this molecule. Therefore, expression of GPA33 seems to provide a diagnostic tool to identify autoimmune disease caused by Treg insufficiency.

REFERENCES

Ayyoub, M., et al., Human memory FOXP3$^+$ Tregs secrete IL-17 ex vivo and constitutively express the T (H) 17 lineage-specific transcription factor RORgamma t. Proc Natl Acad Sci USA, 2009. 106 (21): p. 8635-40.

Bluestone, J. A., et al., Type 1 diabetes immunotherapy using polyclonal regulatory T cells. Sci Transl Med, 2015. 7 (315): p. 315ra189.

Cox, J. and M. Mann, MaxQuant enables high peptide identification rates, individualized p.p.b.-range mass accuracies and proteome-wide protein quantification. Nat Biotechnol, 2008. 26 (12): p. 1367-72.

Feng, Y., et al., Control of the inheritance of regulatory T cell identity by a cis element in the Foxp3 locus. Cell, 2014. 158 (4): p. 749-63.

Heath, J. K., et al., The human A33 antigen is a transmembrane glycoprotein and a novel member of the immunoglobulin superfamily. Proc Natl Acad Sci USA, 1997. 94 (2): p. 469-74.

Himmel, M. E., et al., Helios$^+$ and Helios-cells coexist within the natural FOXP3$^+$T regulatory cell subset in humans. J Immunol, 2013. 190 (5): p. 2001-8.

Hippen, K. L., et al., Massive ex vivo expansion of human natural regulatory T cells (T(regs)) with minimal loss of in vivo functional activity. Sci Transl Med, 2011. 3 (83): p. 83ra41.

Kanamori, M., et al., Induced Regulatory T Cells: Their Development, Stability, and Applications. Trends Immunol, 2016.

Miyara, M., et al., Functional delineation and differentiation dynamics of human CD4$^+$ T cells expressing the FoxP3 transcription factor. Immunity, 2009. 30 (6): p. 899-911.

Pesenacker, A. M., et al., CD161 defines the subset of FoxP3$^+$ T cells capable of producing proinflammatory cytokines. Blood, 2013. 121 (14): p. 2647-58.

Saito, T., et al., Two FOXP3($^+$)CD4($^+$) T cell subpopulations distinctly control the prognosis of colorectal cancers. Nat Med, 2016. 22 (6): p. 679-84.

Sakaguchi, S., et al., Regulatory T cells and immune tolerance. Cell, 2008. 133 (5): p. 775-87.

Thornton, A. M., et al., Expression of Helios, an Ikaros transcription factor family member, differentiates thymic-derived from peripherally induced Foxp3$^+$ T regulatory cells. J Immunol, 2010. 184 (7): p. 3433-41.

Trzonkowski, P., et al., Hurdles in therapy with regulatory T cells. Sci Transl Med, 2015. 7 (304): p. 304ps18.

Wan, Y. Y. and R. A. Flavell, Regulatory T-cell functions are subverted and converted owing to attenuated Foxp3 expression. Nature, 2007. 445 (7129): p. 766-70.

Wisniewski, J. R., et al., A "proteomic ruler" for protein copy number and concentration estimation without spike-in standards. Mol Cell Proteomics, 2014. 13 (12): p. 3497-506.

The invention claimed is:

1. A method for detecting CD4$^+$CD25$^+$ glycoprotein A33 (GPA33)$^{high}$ and/or CD4$^+$CD127$^-$GPA33$^{high}$ T cells in a sample comprising:
   obtaining a cell sample; and
   detecting CD4$^+$CD25$^+$GPA33$^{high}$ and/or CD4$^+$CD127$^-$GPA33$^{high}$ T cells by contacting the cell sample with an anti-CD4 antibody or antigen-binding fragment thereof and an anti-GPA33 antibody or antigen-binding fragment thereof and detecting binding between cells in the sample and the anti-CD4 antibody or antigen-binding fragment thereof and the anti-GPA33 antibody or antigen-binding fragment thereof, and contacting the cell sample with an anti-CD25 antibody or antigen-binding fragment thereof and detecting binding between cells in the sample and the anti-CD25 antibody or antigen-binding fragment thereof to detect CD4$^+$CD25$^+$ GPA33$^{high}$ T cells, and/or contacting the cell sample with an anti-CD127 antibody or antigen-binding fragment thereof and detecting binding or the lack thereof between cells in the sample and the anti-CD127 antibody or antigen-binding fragment thereof to detect CD4$^+$CD127$^-$GPA33$^{high}$ T cells, wherein GPA33$^{high}$ is defined as the expression level of GPA33 that is higher than the average level of expression of GPA33 on CD4$^+$ T cells in the cell sample.

2. A method according to claim 1, wherein said cells are obtained from a tumor or a tumor sample.

3. The method according to claim 1 further comprising quantifying the level of CD4$^+$CD25$^+$GPA33$^{high}$ and/or CD4$^+$CD127$^-$GPA33$^{high}$ cells in said sample.

4. The method according to claim 3, comprising quantifying the level of CD4$^+$CD25$^+$GPA33$^{high}$ cells.

5. The method according to claim 1, further comprising isolating said CD4$^+$CD25$^+$GPA33$^{high}$ and/or CD4$^+$CD127$^-$GPA33$^{high}$ T cells.

6. The method according to claim 5, further comprising culturing the isolated cells in the presence of one or more factors promoting proliferation, activation and/or growth of said cells.

7. The method according to claim 1 wherein CD4$^+$CD25$^+$GPA33$^{high}$ T cells are detected.

8. The method according to claim 1 wherein CD4$^+$CD25$^+$CD127$^-$GPA33$^{high}$ T cells are detected.

9. The method according to claim 1 wherein GPA33$^{high}$ refers to a level of expression that is at least 2-fold the average level of expression of GPA33 on CD4$^+$ T cells in the cell sample.

10. A method for detecting CD4$^+$CD25$^+$ glycoprotein A33(GPA33)$^{high}$ and/or CD4$^+$CD127$^-$GPA33$^{high}$ T cells in a sample, comprising:

obtaining a cell sample; and detecting CD4$^+$CD25$^+$GPA33$^{high}$ and/or CD4$^+$CD127$^-$GPA33$^{high}$ T cells by contacting the cell sample with an anti-CD4 antibody or antigen-binding fragment thereof and an anti-GPA33 antibody or antigen-binding fragment thereof and detecting binding between cells in the sample and the anti-CD4 antibody or antigen-binding fragment thereof and the anti-GPA33 antibody or antigen-binding fragment thereof, and contacting the cell sample with an anti-CD25 antibody or antigen-binding fragment thereof and detecting binding between cells in the sample and the anti-CD25 antibody or antigen-binding fragment thereof to detect CD4$^+$CD25$^+$GPA33$^{high}$ T cells, and/or contacting the cell sample with an anti-CD127 antibody or antigen-binding fragment thereof and detecting binding or the lack thereof between cells in the sample and the anti-CD127 antibody or antigen-binding fragment thereof to detect CD4$^+$CD127$^-$GPA33$^{high}$ T cells, wherein GPA33$^{high}$ is defined as the expression level of GPA33 at which 75% of CD4$^+$CD25$^+$CD45RA$^+$ T cells are GPA33$^+$.

* * * * *